United States Patent
Mairhofer

(10) Patent No.: US 11,120,540 B2
(45) Date of Patent: Sep. 14, 2021

(54) MULTI-VIEW IMAGING SYSTEM AND METHODS FOR NON-INVASIVE INSPECTION IN FOOD PROCESSING

(71) Applicant: THAI UNION GROUP PUBLIC COMPANY LIMITED, Samutsakorn (TH)

(72) Inventor: Stefan Mairhofer, Samutsakorn (TH)

(73) Assignee: THAI UNION GROUP PUBLIC COMPANY LIMITED, Samutsakorn (TH)

( * ) Notice: Subject to any disclaimer, the term of this patent is extended or adjusted under 35 U.S.C. 154(b) by 0 days.

(21) Appl. No.: 16/224,379

(22) Filed: Dec. 18, 2018

(65) Prior Publication Data

US 2020/0193587 A1    Jun. 18, 2020

Related U.S. Application Data

(60) Provisional application No. 62/765,113, filed on Aug. 16, 2018.

(51) Int. Cl.
*H04N 17/00* (2006.01)
*G06T 7/00* (2017.01)
(Continued)

(52) U.S. Cl.
CPC ....... *G06T 7/0004* (2013.01); *G01N 21/3563* (2013.01); *G01N 33/12* (2013.01);
(Continued)

(58) Field of Classification Search
CPC .... G01N 21/3563; G01N 33/12; G06T 17/00; G06T 2200/08; G06T 2207/30128; H04N 5/2256; H04N 5/247
See application file for complete search history.

(56) References Cited

U.S. PATENT DOCUMENTS 5,352,153 A    10/1994 Burch et al.
5,970,424 A *  10/1999 Kaffka ................. G01N 21/359
                                                  702/28
(Continued)

FOREIGN PATENT DOCUMENTS

CN    102141525 A    8/2011
CN    108122265 A    6/2018
(Continued)

OTHER PUBLICATIONS

Boldrini et al., "Hyperspectral imaging: a review of best practice, performance and pitfalls for in-line and on-line applications," *Journal of Near Infrared Spectroscopy* 20:483-508, 2012.
(Continued)

*Primary Examiner* — Dave Czekaj
*Assistant Examiner* — Berteau Joisil
(74) *Attorney, Agent, or Firm* — Seed IP Law Group LLP

(57) ABSTRACT

An inline vision-based system used for the inspection and processing of food material and associated imaging methods are disclosed. The system includes a conveyor belt, a transparent plate, and an imaging system, wherein the imaging system includes a light source and at least one camera. The imaging system produces image data from multiple views of light passing through an object on the transparent plate and captured by the camera. The image data corresponds to one of transmittance, interactance, or reflectance image data and is transmitted to a processor. The processor processes the data using machine learning to generate a three dimensional model of the geometry of a portion of material internal to the object so as to determine boundaries of the portion relative to the surrounding material.

19 Claims, 9 Drawing Sheets

(51) Int. Cl.
| | |
|---|---|
| H04N 5/225 | (2006.01) |
| G06T 17/00 | (2006.01) |
| H04N 5/247 | (2006.01) |
| G01N 33/12 | (2006.01) |
| G01N 21/3563 | (2014.01) |

(52) U.S. Cl.
CPC ........... *G06T 17/00* (2013.01); *H04N 5/2256* (2013.01); *H04N 5/247* (2013.01); *G06T 2200/08* (2013.01); *G06T 2207/20081* (2013.01); *G06T 2207/20084* (2013.01); *G06T 2207/30128* (2013.01)

(56) References Cited

U.S. PATENT DOCUMENTS

| | | | |
|---|---|---|---|
| 6,116,404 A * | 9/2000 | Heuft | B07C 5/122 198/339.1 |
| 6,563,904 B2 | 5/2003 | Wijts et al. | |
| 6,587,575 B1 | 7/2003 | Windham et al. | |
| 7,060,981 B2 | 6/2006 | Retterath et al. | |
| 7,857,686 B2 | 12/2010 | Amason | |
| 8,126,213 B2 | 2/2012 | Chao et al. | |
| 9,095,147 B2 | 8/2015 | Hjalmarsson et al. | |
| 9,176,110 B1 | 11/2015 | Kim et al. | |
| 9,476,865 B2 | 10/2016 | Subbiah et al. | |
| 9,551,616 B2 | 1/2017 | McQuilkin et al. | |
| 2013/0020392 A1* | 1/2013 | Olmstead | G07G 1/0063 235/440 |
| 2014/0203012 A1* | 7/2014 | Corona | H05B 6/6447 219/705 |
| 2019/0311931 A1* | 10/2019 | Cheung | H01L 21/681 |

FOREIGN PATENT DOCUMENTS

| | | |
|---|---|---|
| EP | 2 755 018 A1 | 7/2014 |
| WO | 01/09587 A1 | 2/2001 |
| WO | 03/034059 A1 | 4/2003 |
| WO | 2006/129391 A1 | 12/2006 |
| WO | 2008/016309 A1 | 2/2008 |
| WO | 2017/093539 A1 | 6/2017 |

OTHER PUBLICATIONS

Brosnan et al., "Improving quality inspection of food products by computer vision—a review," *Journal of Food Engineering* 61:3-16, 2004.

Chatfield et al., "Return of the Devil in the Details: Delving Deep into Convolutional Nets," *arXiv preprint arXiv*:1405.3531: 2014, 1 page.

Cheung et al., "Shape-From-Silhouette Across Time | Part I: Theory and Algorithms," *International Journal of Computer Vision* 62(3):221-247, 2005 (51 pages).

Cubero et al., "Advances in Machine Vision Application for Automatic Inspection and Quality Evaluation of Fruits and Vegetables," *Food Bioprocess Technol* 4:487-504, 2010.

Davis (Ed.), *Foundations of Image Understanding*, 2001, Springer Publishing Company, New York, New York, Chapter 16, Dyer, "Volumetric Scene Reconstruction from Multiple Views," pp. 469-489.

Einarsdóttir et al., "Novelty detection of foreign objects in food using multi-model X-ray imaging," *Food Control* 67:39-47, 2016.

Garrido-Jurado et al., "Automatic generation and detection of highly reliable fiducial markers under occlusion," *Pattern Recognition* 47(6):2280-2292, 2014 (14 pages).

Geng, "Structured-light 3D surface imaging: a tutorial," *Advances in Optics and Photonics* 3:128-160, 2011.

Gowen et al., "Hyperspectral imaging—an emerging process analytical tool for food quality and safety control," *Trends in Food Science & Technology* 18:590-598, 2007.

Haff et al., "X-ray detection of defects and contaminants in the food industry," *Sens. & Instrument. Food Qual.* 2:262-273, 2008.

Hu et al., "Classification and characterization of blueberry mechanical damage with time evolution using reflectance, transmittance and interactance imaging spectroscopy," *Computers and Electronics in Agriculture* 122:19-28, 2016.

Karpathy et al., "Large-scale Video Classification with Convolution Neural Networks," *IEEE Conference on Computer Vision and Pattern Recognition*, Columbus, Ohio, Jun. 23-28, 2014, pp. 1725-1732.

Krizhevsky et al., "ImageNet Classification with Deep Convolutional Neural Networks," *Advances in Neural Information Processing Systems*, Lake Tahoe, Nevada, Dec. 3-6, 2012, 9 pages.

Krizhevsky et al., "ImageNet Classification with Deep Convolutional Neural Networks," *Communications of the ACM* 60(6):84-90, 2017.

Li et al., "Towards Total Scene Understanding: Classification, Annotation and Segmentation in an Automatic Framework," *IEEE Conference on Computer Vision and Pattern Recognition*, Miami Beach, Florida, Jun. 20-25, 2009, 8 pages.

Liu et al., "Recent Advances in Wavelength Selection Techniques for Hyperspectral Image Processing in the Food Industry," *Food Bioprocess Technol* 7:307-323, 2013.

Long et al., "Fully Convolutional Networks for Semantic Segmentation," *IEEE Conference on Computer Vision and Pattern Recognition*, Boston, Massachusetts, Jun. 8-10, 2015 pp. 3431-3440.

Mathanker et al., "X-Ray Application in Food and Agriculture: A Review," *Transactions of the ASABE* 56(3): 2013, 17 pages.

Mathiassen et al., "Trends in application of imaging technologies to inspection of fish and fish products," *Trends in Food Science & Technology* 22:257-275, 2011.

Moons et al., "3D Reconstruction from Multiple Images | Part 1: Principles," *Foundations and Trends ® in Computer Graphics and Vision* 4(4):287-398, 2008.

Naganathan et al., "Visible/Near-Infrared Hyperspectral Imaging for Beef Tenderness Prediction," *Computers and Electronics in Agriculture* 64:225-233, 2008.

Newell et al., "Stacked Hourglass Networks for Human Pose Estimation," *European Conference on Computer Vision*, Amsterdam, The Netherlands, Oct. 8-16, 2016, pp. 483-499.

Nicolaï et al., "Nondestructive measurement of fruit and vegetable quality by means of NIR spectroscopy: A review," *Postharvest Biology and Technology* 46:99-118, 2007.

Pereira et al., "Inline discrete tomography system: Application to agriculture product inspection," *Computers and Electronics in Agriculture* 138:117-126, 2017.

Qin et al., "Monte Carlo simulation for quantification of light transport features in apples," *Computers and Electronics in Agriculture* 68:44-51, 2009.

Schreer (Ed.) et al., *3D Video Communications*, 2005, John Wiley & Sons, Chichester, West Sussex, England, Chapter 8, Eisert, "Reconstruction of Volumetric 3D Models," pp. 134-150 (23 pages).

Seitz et al., "A Comparison and Evaluation of Multi-View Stereo Reconstruction Algorithms," *Proceedings of the 2006 IEEE Computer Society Conference on Computer Vision and Pattern Recognition*, Washington, DC, Jun. 17-22, 2006, pp. 519-528.

Simonyan et al., "Very Deep Convolutional Networks for Large-Scale Image Recognition," *International Conference on Learning Representations*, San Diego, California, May 7-9, 2015, 14 pages.

Sture et al., "A 3D machine vision system for quality grading of Atlantic Salmon," *Computers and Electronics in Agriculture* 123:142-148, 2016.

Weyrich et al., "Vision based Defect Detection on 3D Objects and Path Planning for Processing," *Proceedings of the 11th WSEAS International Conference on Robotics, Control and Manufacturing Technology*, Venice, Italy, Mar. 8-10, 2011, pp. 19-24.

Wu et al., "Advanced applications of hyperspectral imaging technology for food quality and safety analysis and assessment: A review—Part II: Applications," *Innovative Food Science and Emerging Technologies* 19:15-28, 2013.

(56) References Cited

OTHER PUBLICATIONS

Wu et al., "Advanced applications of hyperspectral imaging technology for food quality and safety analysis and assessment: A review—Part I: Fundamentals," *Innovative Food Science and Emerging Technologies* 19:1-14, 2013.

Zhang, , "A Flexible New Technique for Camera Calibration," *IEEE Transactions on Pattern Analysis and Machine Intelligence* 22(11):1330-1334, 2000.

\* cited by examiner

MULTI-VIEW IMAGING SYSTEM AND METHODS FOR NON-INVASIVE INSPECTION IN FOOD PROCESSING

BACKGROUND

Technical Field

The present disclosure relates to non-invasive inspection in food processing, and more particularly, to an imaging system and associated methods for detecting an internal object within food by processing image data of the food to determine a three-dimensional model of the internal object.

Description of the Related Art

The food industry operates within narrow margins and is subject to increasing quality control standards. As such, the food processing industry has turned to automated systems to increase processing capacity while meeting higher quality control standards. Aspects of food processing include separation of primary from secondary products and the removal of foreign bodies, among others, so as to increase the added value of the product. However, these aspects are difficult to automate because the boundaries between the primary and secondary products and the foreign bodies are difficult to identify with current systems.

In instances where there is a natural boundary between food materials, such as for solid to liquid interfaces, separating primary from secondary products is often straightforward and requires little physical efforts. In instances where the food materials are interconnected or there are solid to solid interfaces, an active physical intervention, such as cutting, is usually needed. In order to guide and perform such an action, it is advantageous to identify a precise or best possible boundary between the solid to solid interfaces, which in an automated environment, is often realized through a vision-based system. Even if no separation between materials is required, the ability to detect the presence as well as the extent of a certain defect or undesired object can have major benefits to the food inspection or sorting process.

For example, several systems have been developed for various industries, including fish, meat, poultry, fruits, vegetables and grains, as disclosed in U.S. Pat. Nos. 5,352,153, 6,563,904, 9,551,615, 6,587,575, 9,095,147, and the publications WO 2017/093539A1 and WO 2008/016309A1. Conventional systems generally apply conventional imaging for rapid screening of food material in order to obtain information relevant to processing. However, the information derived through such approach is generally limited only to the visible surface of the material.

Alternative technologies have been proposed to provide internal details of an object. Whether data is captured from the surface or within the object, the information is generally provided in a two-dimensional format. For some applications this might be sufficient, either because knowing the depth is not of particular relevance, or because the object's geometry is consistent and thus allows certain assumptions to be made. There are, however, scenarios in which the additional information of the third dimension is of particular importance. For instance, the third dimension information is useful for deriving precise information on the object's alignment or for geometry-dependent processing of irregular shaped objects so as to enable precise separation or removal of irregular shaped objects.

Some solutions geared towards the recovery of three-dimensional ("3D") surface data are limited to a rich description of the outer profile. Others are based on volumetric imaging techniques, such as computed tomography ("CT") or magnetic resonance imaging ("MRI"), provide data regarding internal features of the scanned object, however, such technical solutions have multiple limitations. For example, volumetric imaging technologies lack speed, which is a particularly significant limitation given the narrow margins of the food processing industry. The lack of speed, among other limitations, makes current systems more suitable as random quality control inspection tools rather than as an inline solutions for automated food processing and sorting.

BRIEF SUMMARY

The present disclosure is directed to rapid data acquisition and reconstruction for inline industrial food processing applications that allows for capturing geometric details of food material internal components. Such a system is particularly useful for applications where a full representation of the internal structure, such as one provided by volumetric imaging technologies, is unnecessary, but rather, where the recovery of a rough internal profile and speed are essential. In particular, the systems and methods disclosed herein are directed to the surface to surface combination of two distinct materials, wherein one material forms an outer layer that allows the partial penetration of an arbitrary light spectrum, and a second material, or inner object, that is of particular interest is at least partially enclosed in the outer layer and allows for a different range of penetration or absorption by the arbitrary light spectrum. In general, exemplary implementations of the present disclosure include the use of an imaging system, including light sources and imaging devices to capture image data, and computational steps for reconstruction of the data to determine boundaries of the inner object.

An exemplary implementation of a system for capturing and processing image data of an object to determine boundaries of an inner portion of the object includes: a first conveyor; a second conveyor separated from the first conveyor by a gap; a transparent plate positioned in the gap and coupled to at least one of the first conveyor and the second conveyor; a support ring positioned at least in part in the gap and coupled to at least one of the first conveyor and the second conveyor, the support ring including at least one camera coupled to the support ring; and a first light source coupled to the support ring, wherein during operation, the first light source emits light directed towards the transparent plate.

The implementation may further include: an object positioned on the transparent plate, wherein during operation, the camera receives light passing through the object from the first light source; the object being a tuna fillet and the first light source emitting light at a wavelength that is equal to one of approximately 1260 nanometers, approximately 805 nanometers, or approximately 770 nanometers; a control unit in electronic communication with the camera, the camera capturing light passing through the object and transmitting a signal to the control unit corresponding to image data from the captured light; the image data being one of transmittance image data, interactance image data, or reflectance image data; and the control unit including a processor, the processor using machine learning for detecting boundaries between a first portion of the object and a second portion of the object within the first portion based on the image data received from the camera.

The implementation may further include: the processor passing the image data through a deep convolutional neural network; the deep convolutional neural network receiving the image data and outputting a plurality of silhouettes based on the image data corresponding to the second portion of the object, the processor projecting the silhouettes into a plurality of projections and analyzing an intersection between the plurality of projections to determine a three dimensional shape of the second portion of the object; the support ring including a plurality of cameras coupled to the support ring, each of the plurality of cameras capturing one of transmittance, interactance, or reflectance imaging data from the first light source; and the support ring including a second light source coupled to the support ring, wherein during operation, the second light source emits light directed to the transparent plate.

An alternative exemplary implementation of a device for capturing and processing image data of an object to determine boundaries of an inner portion of the object includes: a conveyor having a space between a first portion and a second portion of the conveyor; a plate positioned in the space and coupled to the conveyor; a support ring positioned at least in part in the space and coupled to the conveyor, wherein during operation, the support ring rotates between at least a first position and a second position; at least one light source coupled to the support ring, wherein during operation, the at least one light source emits light directed towards an object on the plate; an imaging device coupled to the support ring, wherein the imaging device receives light from the at least one light source after the light passes through the object; and a processor in electronic communication with the imaging device, the processor receiving a first set of image data from the imaging device when the support ring is in the first position and a second set of image data from the imaging device when the support ring is in the second position, wherein during operation, the processor outputs a three-dimensional model of an inner portion of the object from the first set of image data and the second set of image data.

The implementation may further include: the processor utilizing machine learning to process the first set of image data and the second set of image data into a plurality of silhouettes and to project the plurality of silhouettes into a plurality of projections, wherein the three-dimensional model is based on an intersection between each of the plurality of projections; a second light source coupled to the support ring, the imaging device capturing a third set of image data from the second light source when the support ring is in the first or second position, the processor utilizing the third set of image data to clarify boundaries of the three-dimensional model; the imaging device comprising a spectrograph and the at least one light source emitting light at a wavelength selected from one of approximately 1260 nanometers, approximately 805 nanometers, or approximately 770 nanometers.

An exemplary implementation of a method for capturing and processing image data of an object to determine boundaries of an inner portion of the object includes: emitting light from a light source, the emitting including directing the light through an object having a first portion and second portion, the second portion enclosed within the first portion; capturing light from the light source after the light passes through the object with an imaging device, the captured light corresponding to image data of the first portion and the second portion received by the imaging device; transmitting the image data to a processor; and analyzing the image data with the processor to detect a boundary between the first portion and the second portion, wherein the analyzing includes utilizing machine learning to produce a three dimensional representation of the second portion.

The implementation may further include: emitting light from the light source includes emitting the light with a wavelength selected from one of approximately 1260 nanometers, 805 nanometers, or 770 nanometers; utilizing machine learning to produce the three dimensional representation of the second portion includes the machine learning utilizing a deep convolutional neural network for processing the image data; analyzing the image data with the processor includes utilizing machine learning to output a plurality of two dimensional silhouettes corresponding to the image data of the second portion; analyzing the image data with the processor includes utilizing machine learning to create a plurality of projections, wherein each projection corresponds to a respective one of the plurality of two dimensional silhouettes; and analyzing includes utilizing machine learning to produce a three dimensional representation further includes analyzing an intersection between each of the plurality of projections to output a three dimensional representation of the second portion of the object.

BRIEF DESCRIPTION OF THE SEVERAL VIEWS OF THE DRAWINGS

For a better understanding of the implementations, reference will now be made by way of example only to the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be enlarged and positioned to improve drawing legibility. Further, the particular shapes of the elements as drawn are not necessarily intended to convey any information regarding the actual shape of the particular elements, and may have been selected solely for ease of recognition in the drawings.

DETAILED DESCRIPTION

Figure 1:
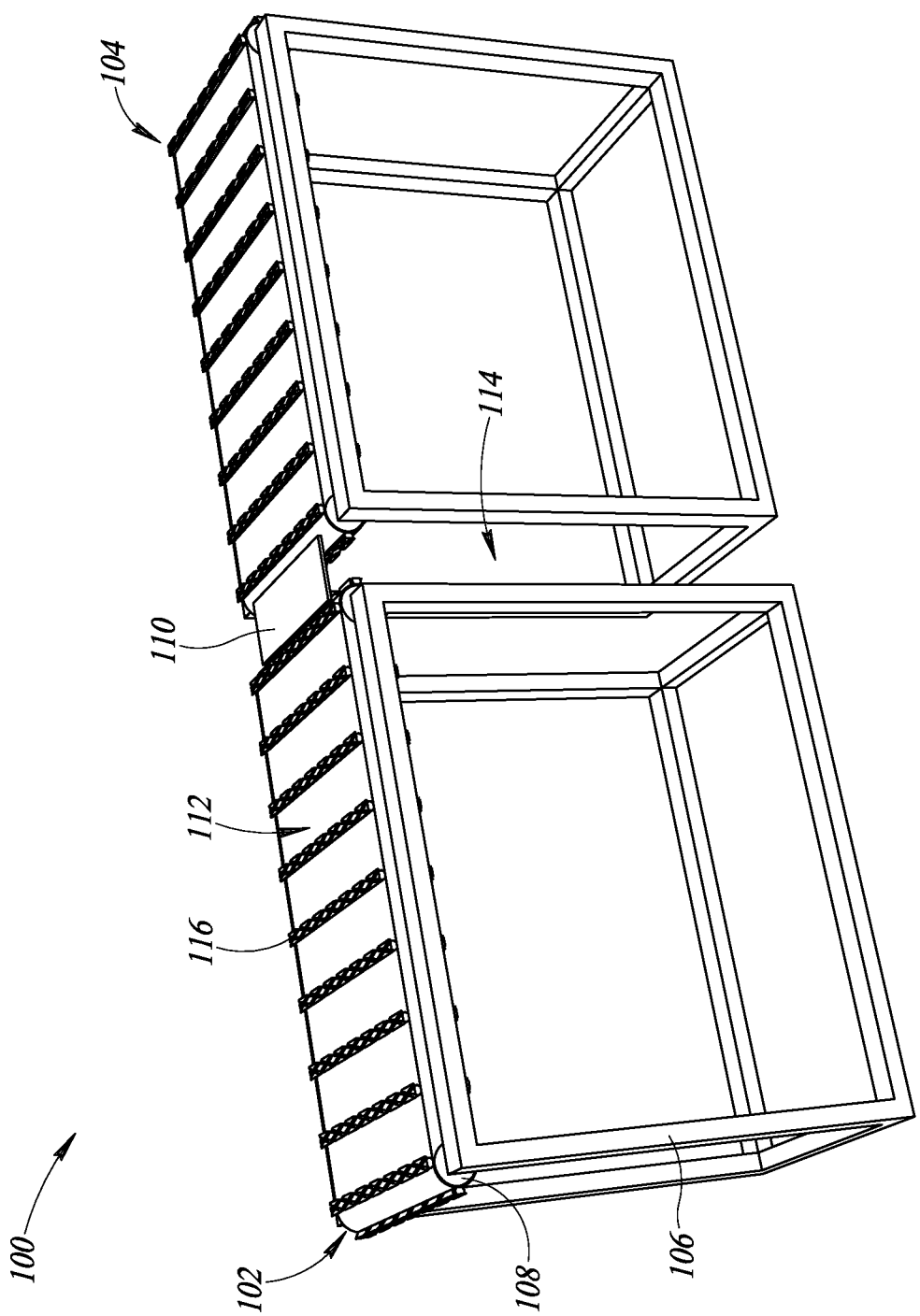
FIG. 1 is a perspective view of an exemplary implementation of a conveyor belt system according to the present disclosure with a gap between a first conveyor and a second conveyor of the system.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with imaging systems, non-invasive inspection in food processing, machine learning, and neural networks have not been shown or described in detail to avoid unnecessarily obscuring descriptions of the implementations.

Unless the context requires otherwise, throughout the specification and claims which follow, the word "comprise" and variations thereof, such as, "comprises" and "comprising" are to be construed in an open, inclusive sense, that is as "including, but not limited to." Further, the terms "first," "second," and similar indicators of sequence are to be construed as interchangeable unless the context clearly dictates otherwise.

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The relative terms "approximately" and "substantially," when used to describe a value, amount, quantity, or dimension, generally refer to a value, amount, quantity, or dimension that is within plus or minus 3% of the stated value, amount, quantity, or dimension, unless the content clearly dictates otherwise. It is to be further understood that any specific dimensions of components provided herein are for illustrative purposes only with reference to the exemplary implementations described herein, and as such, the present disclosure includes amounts that are more or less than the dimensions stated, unless the context clearly dictates otherwise.

The present disclosure provides a solution for a fast and non-invasive imaging system that is able to acquire visual data of food material for processing and inspection. In particular, the implementations of the present disclosure capture the three-dimensional geometry of an arbitrarily-shaped object enclosed by a different layer of material. For example, in implementations where the object to be analyzed is a fish fillet, the imaging systems and methods disclosed herein capture the three-dimensional geometry of a portion of dark meat (e.g., a different layer of material) that is contained within an outer layer of white meat, wherein the dark meat has an arbitrary three-dimensional shape that varies between successive fillets.

Implementations of the present disclosure include various systems, devices, and related methods that can leverage the optical properties of absorption, reflection, transmission and scatter, which differ for different turbid materials and spectral bands. The relative proportion and amount of each occurrence can depend on the chemical composition and physical parameters of the material. When light interacts with matter, a certain portion of photons are reflected, either through specularity, diffusion or backscatter. The first two, specularity and diffusion, depend on the roughness of the surface, while scattering or backscattering of light results from multiple refractions at phase changes or different interfaces inside the material. Scattering may also appear due to heterogeneities, such as pore spaces or capillaries randomly distributed throughout the material, as well as the size, shape and microstructure of different particles.

The remaining photons that are not reflected are either being absorbed or transmitted through the material. The lower the absorption coefficient the deeper light can penetrate into a material before photons are being absorbed, and thus the higher is the probability that light exits the opposite side of the material. Therefore, for non-invasive imaging according to the various implementations of systems, devices, and related methods described herein, both light that is scattered and light that passes through the material can provide useful information of internal properties. Such information, e.g., light that is scattered and light that passes through the material, is captured through interactance or transmittance imaging respectively, while reflectance imaging focuses mainly on the light directly reflected from the surface, as described herein with reference to exemplary implementations.

The optical properties and the results from interacting with turbid materials differ for each wavelength of light. While some wavelengths are quickly absorbed, others can penetrate deep into the material and, depending on the thickness, are able to be fully or partially transmitted. As described in more detail below, some of the implementations of systems, devices, and related methods can include a multi- or hyperspectral imaging tool to investigate the phenomena of optical properties in respect to different wavelengths of the ultraviolet (UV), visible and near infrared (NIR) light spectrum.

Further, some implementations described herein may include or utilize diffraction grating, where light is dispersed and the intensity of each wavelength is captured by various implementations of sensor(s) described herein. Still further, the implementations of systems, devices, and related methods described herein are capable of acquiring associated data which may include or comprise a three-dimensional cube with spatial data stored in two dimensions and the spectral data in the third dimension. The choice of individual or a combination of suitable wavelengths can be varied depending on the processed food material and may be determined in advance. For example, the choice of suitable wavelengths may be selected based on a database which includes transmittance and reflectance information for a particular food to be scanned and a database with spectral properties of certain wavelengths of light, or before processing, the system can be calibrated to determine a wavelength that corresponds to capturing appropriate imaging data based on the particular object or food to be scanned.

In the various implementations of systems, devices, and methods described herein, certain wavelengths are selected which have good penetration abilities through the outer layer of the material with a low absorption coefficient and minimal scatter, while being distinct from the inner object of interest (e.g., white and dark meat of a tuna fish fillet, respectively). Moreover, in the various implementations of systems, devices, and related methods described herein, in addition to selecting appropriate wavelengths suitable for food material inspection, appropriate illumination source can also be selected as a system design variable. For example, light sources can differ in the intensity of emitted light for specific spectrums. Thus, the light source with the wavelengths suitable for the application can be selected in order to achieve optimal results. Several types of illumination sources are disclosed herein, including halogen, LED, and laser lights of particular wavelengths.

The acquisition of high-quality image data of the inspected food material is an aspect of the present disclosure. As described above, although the material being processed is three-dimensional, traditional imaging sensors tend to lack the means of comprehending the depth of a scene, which limits the ability to perceive the complexity of real-world objects. In order to build a three-dimensional representation of an object, the various implementations of systems, devices, and related methods described herein are capable of capturing a collection of images carrying information from multiple views. Unlike a full 3D representation obtained through volumetric imaging technologies, 3D surface reconstruction techniques of conventional imaging systems tend to only capture the 3D coordinates of individual points located on the surface of an object, or in this case, the boundary between two materials of the object. Therefore, such methods are often referred to as surface measurement, range sensing, depth mapping, or surface scanning, which may be used interchangeably herein, unless the context clearly dictates otherwise.

One conventional technique directed to 3D surface reconstruction is multi-view stereo ("MVS"), which matches corresponding feature points in images given sufficient overlap between views. The result is a 3D point cloud to which a surface can be fitted. Such an approach generally requires a feature-rich texture, which texture may not be available or present with certain types of food. In addition, MVS is lacking in efficiency for certain applications in the food processing industry due to the small margins involved therein.

Structured-light 3D surface reconstruction techniques are another technique for acquiring three-dimensional information. Structured-light methods use a spatially varying 1D or 2D structured illumination that is projected on an object. In a planar scene, the illuminated pattern is identically projected onto the surface, while in a non-planar scene the pattern as seen by the camera will be distorted. 3D information is extracted from the characteristics of the distorted pattern, which is usually acquired from the direct reflection of light at the surface boundary.

While both approaches can provide a detailed description of the 3D surface, neither of them would be practical for non-invasive imaging data captured either through interactance or transmittance mode. Shape from silhouettes, on the other hand, relies on the contours of an object, from which a three-dimensional representation can be recovered. As described in more detail below, various implementations of the systems, devices, and related methods are operable to project the silhouettes seen by each camera back into the three-dimensional scene, extracting a 3D shape from their intersections. Because concavities are generally not visible in silhouettes and are therefore disregarded, the reconstruction is only an approximation of the true 3D geometry, commonly known as the visual hull. However, according to the various implementations described herein, using interactance imaging along with transmittance imaging, precise 3D shapes of the objects can be extracted by accounting for the concavities.

As described in more detail below, an aspect in the context of 3D shape reconstruction and the acquisition of multi-view image data is the positioning of cameras. For projecting the silhouettes back into the scene, it is important to determine where the cameras were positioned and how the scene was originally projected onto the image plane. The various systems, devices, and related methods described herein can operate to receive and/or process this information from camera calibrations. Such information can include intrinsic parameters, which are related to how light is being projected through the lens onto the imaging sensor and any distortions occurring through this process, as well as the extrinsic parameters referring to the position of the camera in the real world. The systems, devices, and related methods described herein are capable of implementing a calibration process, including the intrinsic parameters discussed above, for each camera and position contributing to the system's multi view image data acquisition, and can be efficiently achieved by the use of binary fiducial markers.

In some implementations, when acquiring image data, the silhouette of the target object can be determined before a three-dimensional model is generated. For example, an aspect of the present disclosure can include recognizing what in the image data is representing the food material, and then to distinguish between the different components forming the outer and inner layer. For example, in an implementation where the object is fish fillet, the outer layer or first portion corresponds to a first type of meat and the inner layer or second portion corresponds to a second type of meat, which is usually enclosed within the first type of meat. In some aspects, machine learning, more specifically artificial neural networks, can be implemented in carrying out such tasks.

For example, in a neural network there are several nodes in different layers linked through connections associated with weights. These weights are usually adjusted and learnt through several iterations by specifying what output of a node is expected, given a known input. By collecting a large dataset of labeled images, indicating the food material and the internal defect or object of interests, a deep convolutional neural network can be trained to learn how to recognize the location and exact boundaries of specific objects. With an increasing set of training data and a careful design of the neural network architecture, even complex tasks can be efficiently solved using the various systems, devices, and related methods described herein. Moreover, in some implementations, various different models can be implemented for different specific application.

As described herein, the present disclosure incorporates a conveyor belt system for the detection and extraction of the three-dimensional geometry of inspected defects or processed products. Due to the continuous moving belt, it is preferable that data acquisition and analysis are highly efficient. In some implementations, the wavelengths of the applicable light spectrum can be determined beforehand based on the food material and objectives of the application. Specific spectral bands can either be acquired through hyperspectral imaging or the use of specific filters or laser light, which implicates a line scan system.

As described in more detail below, to acquire transmittance data, a light source is positioned opposite of the imaging sensor, which requires a small gap in the conveyor belt bridged by a transparent medium that allows light to be transmitted and passed through the food material. Another light source is positioned next and parallel to the imaging sensor for an interactance imaging mode. Both imaging modes are alternated at high frequency so as to avoid obscuring the image data captured by each mode.

As described in more detail below, in the present disclosure, a combination of multiple light sources and camera sensors (which, as described in more detail herein may be a component of an imaging device or, alternatively, may be generally referred to as an imaging device or in some implementations, a separate component coupled to the imaging device) are mounted in or around a conveyor belt to collect image data from multiple views. Alternatively, in some implementations, a single camera sensor or imaging device can be used instead. However, in such implementations the single camera can be mounted on a rotating frame that allows repositioning light and camera around the conveyor belt. At high conveyor belt speed or reduced acquisition time due to repositioning of the camera system, image data is acquired in a helical alignment. As such, the helical image data is interpolated between acquisition points along the transversal path. The number of views may vary depending on the application and the required detail of the target object. A structure is built around the imaging apparatus, blocking any light from outside, in order to control the illumination during imaging and thus to achieve better image quality.

The present disclosure, in some implementations, uses a deep convolutional neural network trained to detect the location and boundaries of the target object. However, upon review of the present disclosure, it should be understood that the application of the deep convolutional neural network can depend and vary based on the application, and such a model may be trained beforehand in order to accomplish this task. As described in more detail below, the extracted silhouettes are used to generate a rough approximation of the target object's three-dimensional shape. As should be understood, upon review of the present disclosure, the resolution of the reconstructed model is a trade-off between the required speed and details for the intended application. For example, in some implementations, a higher resolution may require a larger number of images and more computational resources for the reconstruction, which in turn affects application speed.

In other implementations, the arrangement and number of cameras may vary, as described herein. Positions and camera parameters can be calibrated prior to capturing image data. Due to the movement of food material on the conveyor belt, the transversal positions of the cameras change in reference to the transported material. The transversal position can be internally maintained, or if necessary depending on application, set in reference to the material or explicitly defined though markers on the conveyor belt.

Turning now to the illustrated exemplary implementations, FIG. 1 is a perspective view of a conveyor system 100.

It is to be appreciated that conveyor system 100 has been simplified for ease of understanding implementations of the instant disclosure and as such, certain features associated with conveyor system 100 have not been described. Conveyor system 100 includes a first conveyor 102 spaced from a second conveyor 104. In other words, a space or gap 114 separates the first conveyor 102 from the second conveyor 104. The first conveyor 102 may generally be referred to herein as a first portion of the conveyor system 100 and similarly, the second conveyor 104 may generally be referred to herein as a second portion of the conveyor system 100. Moreover, the space or gap 114 and a size and shape of a plate 110 can vary according to the specific application and as such, the present disclosure is not limited by the distance between the conveyors 102, 104 corresponding to the space or gap 114 nor by a size or a shape of the plate 110.

The plate 110 is positioned in, or proximate to, the gap 114 so as to form a continuous conveyor line. Preferably, the plate 110 is transparent so as to allow light to pass through the plate 110 without obstruction. For example, the plate 110 may be formed from transparent plastics, polymers, or glass, among others, while in alternative implementations, the plate 110 is translucent and is similarly formed from a translucent plastic, polymer, or glass, for example. The plate 110 is coupled to the conveyor system 100, or more specifically, to at least one of the first conveyor 102 and the second conveyor 104. Moreover, each conveyor 102, 104 of the system 100 is supported by a support structure 106, wherein a conveyor surface 112 translates via rollers 108 and a conventional drive mechanism (not shown). In addition, the conveyor surface 112 may be solid, or may include a plurality of perforations 116, either arranged in a line, as illustrated in FIG. 1, or evenly dispersed across the conveyor surface 112. In other implementations, the conveyor surface 112 is solid, meaning that there are no such perforations in the surface 112.

Figure 2:
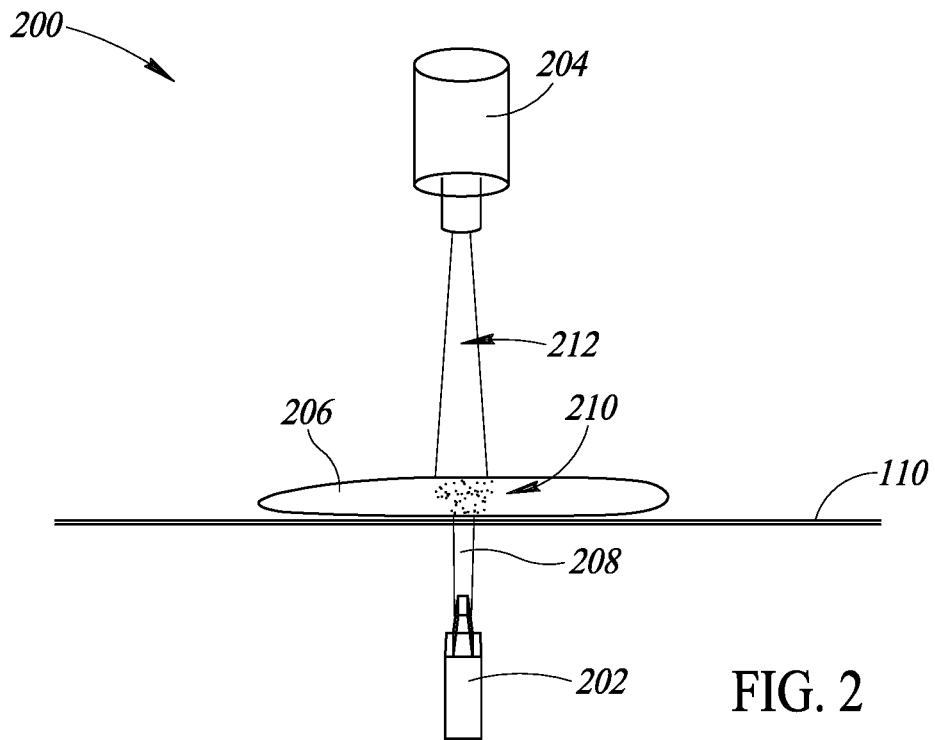
FIG. 2 is a schematic representation of an exemplary implementation of an imaging system according to the present disclosure illustrating a transmittance imaging mode.

FIG. 2 is a schematic representation corresponding to a transmittance imaging mode 200. The transmittance imaging mode 200 includes a light source 202 and an imaging device 204. FIG. 2 further illustrates an object 206 to be scanned, wherein the object 206 is positioned on the plate 110. The light source 202 emits light 208, which is directed towards plate 110 and propagates outward as it travels toward plate 110. As the light 208 transmits through the plate 110 and the object 206, the light converges, as indicated by convergence path or portion 210. When the light 208 exits the object 206, the light 208 diverges or disperses, as illustrated by divergence path or portion 212. After exiting the object 206, the light 208 is captured by the imaging device 204. As described herein, the imaging device 204 receives transmittance image data corresponding to captured light 208 that has been transmitted through the object 206, wherein the transmittance image data is subsequently transmitted via a signal to a processor or control unit in electronic communication with the imaging device 204 for further processing and reconstruction (e.g., control unit 428 illustrated in FIG. 5).

In the illustrated implementation, the conveyor system 100 is generally translating the object 206 from right to left relative to the orientation shown in FIG. 2, although it is to be appreciated that the conveyor system 100 could be translating in either direction. Moreover, the imaging device 204 and the light source 202 are preferably aligned along a vertical axis, wherein the imaging device 204 is above the light source 202, such that the light 208 output by the light source 202 propagates through the object 206 in a linear manner towards the imaging device. It is also to be understood that due to minor variations in alignment or the properties of the object 206 and the light 208, the alignment of the imaging device 204 and the light source 202 may not be truly vertical, but rather may be within 10 degrees of vertical, within 5 degrees of vertical or substantially vertical (i.e. within 3 degrees of vertical).

The light source 202 may be selected from one of a variety of sources in various implementations, such as a laser, a light emitting diode ("LED"), an array or panel of LEDs, incandescent lamps, compact fluorescent lamps, halogen lamps, metal halide lamps, fluorescent tubes, neon lamps, low pressure sodium lamps, or high intensity discharge lamps, for example. In implementations where the light source 202 is a laser, implementations of the present disclosure further include the light source 202 comprising a solid state, gas, excimer, dye, or semiconductor laser. To the extent that the laser is characterized by the duration of laser emission, the laser may also be a continuous wave, single pulsed, single pulsed q-switched, repetitively pulsed, or mode locked laser.

Moreover, as discussed above, the light source 202 is preferably selected specifically for the application or object 206 to be scanned, as different light sources 202 output light 208 with different penetration characteristics relative to object 206. In an implementation where the object 206 is a fish fillet, the light source 202 preferably outputs light in the transmittance imaging mode 200 with a wavelength of between 790 and 820 nanometers ("nm"), but more preferably, the wavelength is 805 nm or approximately 805 nm (i.e. between 800 and 810 nm), which corresponds to wavelengths in the infrared portion of the electromagnetic spectrum that is outside of the visible light portion of the spectrum generally between approximately 400 and 750 nm. Moreover, this wavelength corresponds, at least with respect to a tuna fillet, to a wavelength of light that allows for deep penetration into the fillet while minimizing scatter, wherein scatter is generally undesirable in the transmittance imaging mode 200, as scatter tends to reduce the accuracy of the image data corresponding to the transmittance imaging mode 200.

The near-infrared spectrum at greater than 750 nm or approximately 805 nm is useful for tuna processing because water is still somewhat transparent to these wavelengths as is hemoglobin, which contributes to a substantial part of the biological tissue in a tuna fish fillet. Comparatively, in the visible spectrum (i.e. 400 nm to 750 nm), hemoglobin absorbs most of the light. One potential explanation as to why the light penetrates the white meat but not the dark meat at these wavelengths is due to the different density of the muscle fibers between the two materials, wherein the density of muscle fibers for the dark meat is much higher than the white meat. The absorption coefficient for the dark meat in this range of wavelengths (i.e. near-infrared or approximately 805 nm) is still very high, whereas the absorption coefficient for the white meat is lower. Besides physical properties, these characteristics can also be explained by differences in chemical compositions, for example. As such, for the white meat, the penetration remains rather deep. This difference in behavior makes this particular choice of wavelengths (i.e. approximately 805 nm) preferable for applications where the object to be scanned is a tuna fish fillet.

In certain implementations, the imaging device 204 is one of a number of commercially available imaging devices 204, including, without limitation, a spectrograph, a camera, or a sensor, among others. In implementations where the imaging device 204 is a sensor, the imaging device 204 is preferably a complementary metal oxide semiconductor ("CMOS") sensor that captures wavelengths between 300 nm and 1000 nm. Alternatively, in other implementations, the sensor is a charged-coupled device ("CCD") that captures similar wavelengths sensor or an indium gallium arsenide ("InGaAs") sensor, which captures wavelengths between 900 and 1700 nm. It is to be further appreciated that in implementations where the imaging device 204 is a camera or a spectrograph, that the camera or spectrograph can include any of the above sensors, in addition to other electronic components and other types of sensors.

In calibrating the transmittance imaging mode 200, or altering the mode 200 for different applications, the light 208 is preferably split into individual wavelengths so as to investigate which wavelengths have the best transmittance and capture properties for the object 206. Although not specifically illustrated, a spectrograph with a diffraction grating can be used to split the light 208 into individual wavelengths. Alternatively, because spectrographs are sensitive and expensive, once the mode 200 is calibrated, a blocking filter that only allows certain selected wavelengths of light to pass through to be captured by the imaging device 204 that correspond to the application can be used in order to increase efficiency and reduce cost. As yet a further alternative, a laser light source 202 can be used that only emits light with a specified wavelength, or in a specified wavelength range, that preferably corresponds to the preferred wavelength selected through calibration, which again, results in reduced cost and increased efficiency. By comparison, blocking filters usually have a wider range of pass-through wavelengths, while lasers are very specific to a particular wavelength and as such, selecting between the two will depend on the desired operational wavelength for the material in question.

Figure 3:
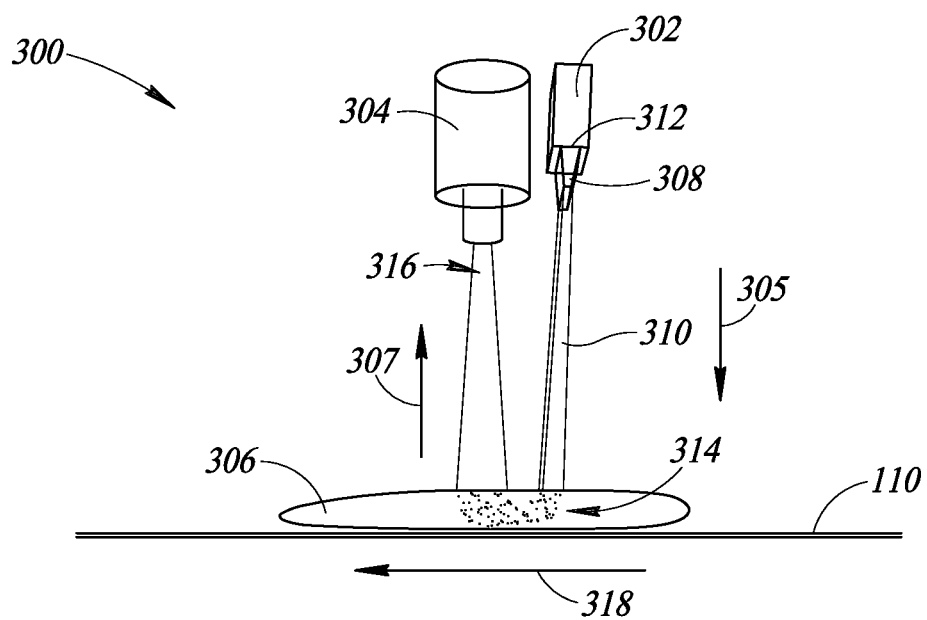
FIG. 3 is a schematic representation of an exemplary implementation of an imaging system according to the present disclosure illustrating an interactance imaging mode.

FIG. 3 is a schematic representation of an exemplary implementation of an interactance imaging mode 300. The interactance imaging mode 300 includes a light source 302 and an imaging device 304. In some implementations, the imaging device 304 may be different than the imaging device 204 of the transmittance mode; in some implementations, the imaging device 304 of the interactance imaging mode 300 may be the same as the imaging device 204 of the transmittance mode. In other words, the same imaging device can be used for both transmittance imaging and interactance imaging modes. The light source 302 and the imaging device 304 may be any of the light sources and imaging devices described above with reference to light source 202 and imaging device 204, respectively. An object 306 to be scanned is present on plate 110 and the light source 302 emits light 310. However, as compared to the transmittance imaging mode 200, in the interactance imaging mode 300, the light 310 passes through a convergence lens 308 coupled to the light source 302 at an output 312 of the light source 302. The convergence lens 308 may be any of a number of known convergence lenses with principal axis, focal points, focal lengths, and vertical plans selected according to the specific application. The convergence lens 308 assists with clarifying image data captured by the imaging device 304, among other benefits.

In the interactance imaging mode 300 for implementations where the object 306 is a fish fillet, and more specifically a tuna fillet, the light source 302 preferably emits light at a wavelength that is between 740 and 800 nm and more preferably, is 770 nm or approximately 770 nm (i.e. between 765 and 775 nm). Further, the imaging device 304 is preferably, or preferably includes, a sensor a CMOS or a CCD sensor as described herein. This range of wavelengths has been found to be preferable for the interactance imaging mode 300 based on the above analysis with respect to the preferable wavelengths of the transmittance imaging mode 200.

After the light 310 is emitted by the light source 302 and passes through convergence lens 308, the light 310 contacts the object 306 as indicated by the portion 314 of light 310 passing through the object 306. However, in the interactance imaging mode, the imaging device 304 measures light that is backscattered by the object 306. In other words, portion 314 of the light 310 corresponds to light that enters object 306 and then bends, curves, or turns within the object 306 due to the material composition of the object 306 and the light 310 before exiting the object 306. In other words, the light 310 that is emitted through the convergence lens 308 propagates along a first direction 305 and the light 310 exiting the object propagates in a second direction 307, wherein in an implementation, the first and second directions are opposite each other along parallel axis. However, it is to be appreciated that implementations of the present disclosure also include the first and second directions being at an angle transverse to each other, such as when the light source 302 is at an angle with respect to the object 306, as described with reference to FIG. 4. The light 310 exits the object 306 and propagates toward the imaging device 304, wherein during propagation, the light disperses as indicated by the dispersing portion 316. When the light 310 is received by the imaging device 304, the imaging device 304 transmits interactance imaging data corresponding to an amount of captured light 310 to a control unit or processor, as described herein (e.g., control unit 428 illustrated in FIG. 5).

In the illustrated implementation, the conveyor 100 is generally translating the object 306 from right to left relative to the orientation shown in FIG. 3, as indicated by arrow 318. As such, the light source 302 is located upstream of the imaging device 304 relative to the direction of translation of the conveyor system 100. In other words, the light source 302 is generally located proximate to and preferably parallel to the imaging device 304. While it may be possible to have the light source 302 downstream from the imaging device 304, this arrangement would result in less accurate imaging data that would have to be corrected during processing. Moreover, it is also possible for the conveyor 100 to translate the object 306 opposite to the direction indicated by arrow 318, in which case, the light source is preferably to the left (i.e. upstream) of the imaging device 304 in the illustrated orientation. In addition, both the light source 302 and the imaging device 304 are located above the object 306, and as such, the interactance imaging mode 300 captures the portion 314 of light 310 that scatters back towards the imaging device 304 after it enters the object 306, as opposed to the transmittance imaging mode 200, which captures the portion of light that translates directly through the object 206 along a substantially vertical axis.

Figure 4:
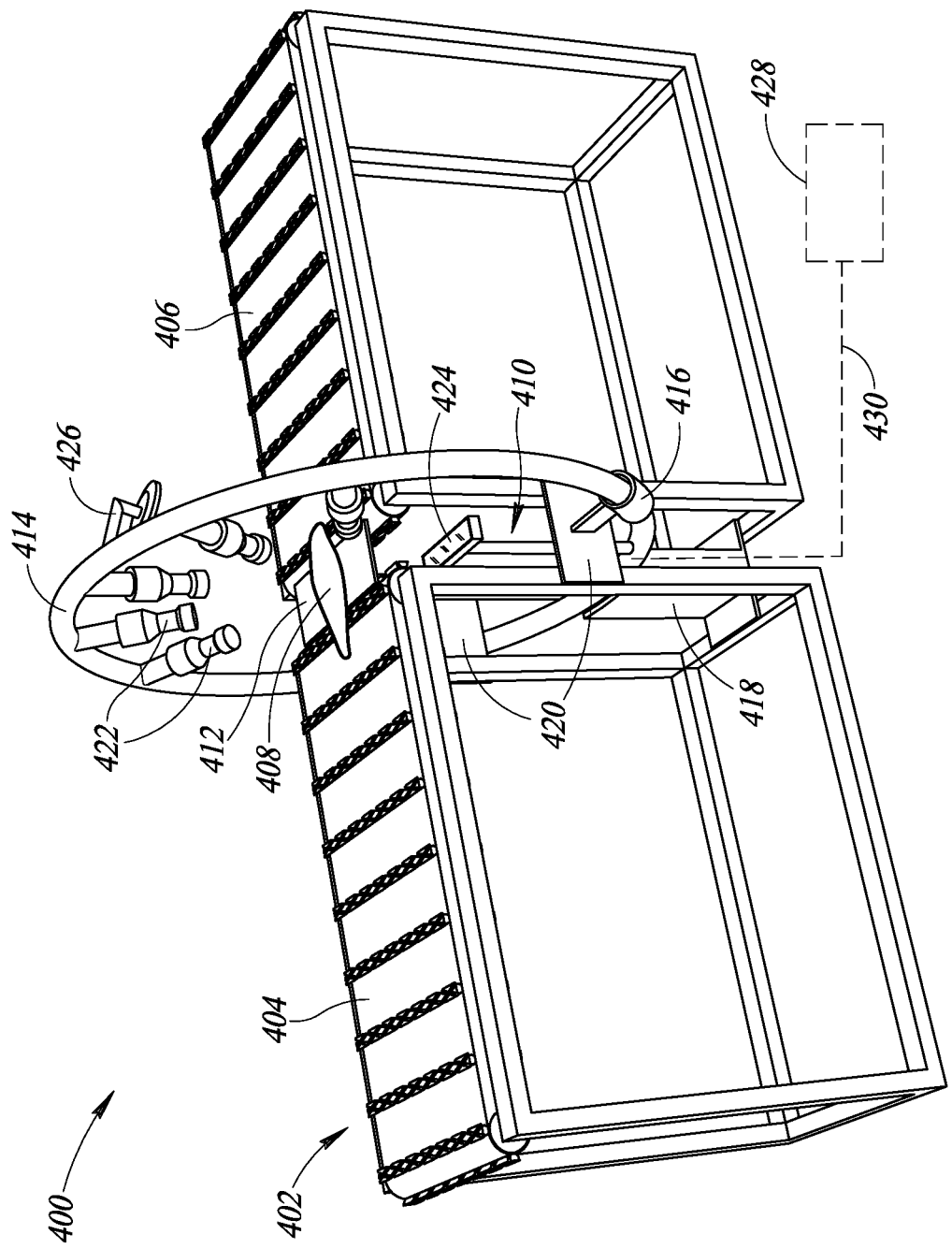
FIG. 4 is a perspective view of an exemplary implementation of an imaging system according to the present disclosure having a support ring and a plurality of imaging devices and light sources coupled to the support ring.

FIG. 4 illustrates a perspective view of an exemplary implementation of an imaging system 400 including a conveyor system 402, a support ring 414 coupled to the conveyor system 402, a plurality of imaging devices 422 coupled to the support ring 414, and at least one light source, such as first light source 424, coupled to the support ring 414.

The conveyor system 402 may include all or substantially of the features described above with reference to conveyor system 100 in FIG. 1. However, briefly, the conveyor system 402 includes a first conveyor or portion 404 and a second conveyor or portion 406, wherein the first conveyor 404 is separated from the second conveyor 406 by a gap or space 410. A plate 412, which is preferably transparent, is positioned in the gap 410 and coupled to the conveyor system 402 so as to form a continuous conveyor line.

As described above, the support ring or frame 414 is coupled to the conveyor system 402 with supports 416, 418, wherein the support ring 414 is preferably circular so as to facilitate rotation of the support ring 414 during calibration of the imaging system 400. The supports 416 are preferably an adjustable collar coupled to and extending from plates 420 coupled to the conveyor system 402, and more specifically, each of the first and second conveyors 404, 406. The support 418 is preferably a base with an open channel for receiving the support ring 414 that is coupled to the conveyor system 402, such that the support ring 414 can be manually rotated by adjusting support collars 416 during calibration of the system. Although support 416 is illustrated as a collar and support 418 is illustrated as a base with a channel for receiving the support ring 414, it is to be appreciated that a number of other devices or arrangements are considered in the present disclosure for coupling the support ring 414 to the conveyor system 402. For example, in other implementations, the coupling includes use of one or more centrally disposed spokes extending from the conveyor system 402 or another structure located in the space 410 and coupled to the conveyor system 402, or alternatively, the support ring 414 can be coupled to and supported by a housing, such as the housing illustrated in FIG. 6.

The support ring 414 further includes a plurality of imaging devices 422 coupled to and extending from the support ring 414. Each of the imaging devices 422 can be substantially similar, if not identical to the imaging device 204 described with reference to FIG. 2 and any variations thereof. In addition, the support ring 414 includes at least a first light source 424, which may be any of the light sources discussed above with reference to light source 204 in FIG. 2. As shown in FIG. 4, the first light source 424 is positioned between the conveyor system 402 and arranged such that light emitted by the first light source 424 is directed toward the plate 412 and an object 408 on the plate 412 to be imaged or scanned. The light passes through plate 412, the object 408, to be received by at least one of the plurality of imaging devices 422, wherein data corresponding to the light received from the first light source 424 corresponds to transmittance imaging data.

In the illustrated implementation, the support ring further includes a second light source 426 coupled to and extending from the support ring 414 proximate the plurality of imaging devices 422. Preferably, the second light source 426 is used in the interactance imaging mode, wherein the second light source 426 is located proximate and parallel to the imaging devices 422. In yet further embodiments, the second light source 426 is located proximate to the imaging devices 422, but is at an angle that is transverse to a field of vision of the imaging devices 422, as illustrated in FIG. 4 and described herein. The second light source 426 may similarly be any of the above light sources discussed with reference to light source 202 in FIG. 2. The second light source 426 emits light that corresponds to the interactance imaging mode 300 described with reference to FIG. 3. As such, light emitted by the second light source 426 is directed towards the object 408 in a first direction, turns within the object 408, and exits the object 408 in a second direction to be received by at least one, if not all, of the plurality of imaging devices 422, wherein data corresponding to the light received from the second light source 426 corresponds to interactance imaging data. In the illustrated embodiment, the angle between the first and second directions is less than 90 degrees and preferably less than 45 degrees, although it is to be understood that the angle will vary according to the specific application (i.e. the type of object 408 to be scanned).

As shown in FIG. 4, the plurality of imaging devices 422 includes 5 imaging devices 422, wherein the imaging devices 422 are equally spaced from one another along a perimeter, circumference, or inner edge of the support ring 414 with an input directed towards the plate 412 and the object 408 for receiving light from one of the light sources 424, 426. As such, each of the imaging devices 422 will receive imaging data corresponding to different views of the object 408. In other words, there will be variance between the views or data from each of the imaging devices 422 due to the arrangement, which assists with producing silhouettes and three-dimensional image data of the object 408. Thus, in the illustrated implementation, it is not necessary to rotate the support ring 414 during normal operation, as the selection and arrangement of the plurality of imaging devices 422 provide for multiple views that are input to a machine learning system, wherein the machine learning system generates silhouettes that are the basis for determining a 3D model based on the multiple views, as described herein. However, it is to be appreciated that the specific number, arrangement, and orientation of imaging devices 422 depends on the object 408 to be scanned and the calibration of the system 400, as discussed herein.

Moreover, each of the imaging device 422 can receive reflectance imaging data from the second light source 426, wherein the reflectance imaging data corresponds to the second light source 426 outputting light at a wavelength that is between 1230 and 1290 nm, or more preferably, is 1260 nm or approximately 1260 nm (i.e. between 1255 and 1265 nm), wherein light emitted at this wavelength is reflected off an outer surface of the object 408 to be received or captured by the plurality of imaging devices 422. This wavelength (i.e. approximately 1260 nm) is preferable for a reflectance imaging mode because although water becomes highly absorbent for wavelengths above 1000 nm, the dark meat starts to reflect the light at approximately 1260 nm, whereas the white meat does not. In a reflectance imaging mode, each of the imaging devices 422 may further include an InGaAs sensor, as described above, for capturing light at this larger wavelength. Reflectance imaging data is particularly useful in situations where an object is only partially contained within an outer layer (i.e. a portion of the object extends out of the outer layer), but in other implementations, reflectance imaging data can be used, in addition to interactance imaging data, as a correction reference.

Figure 5:
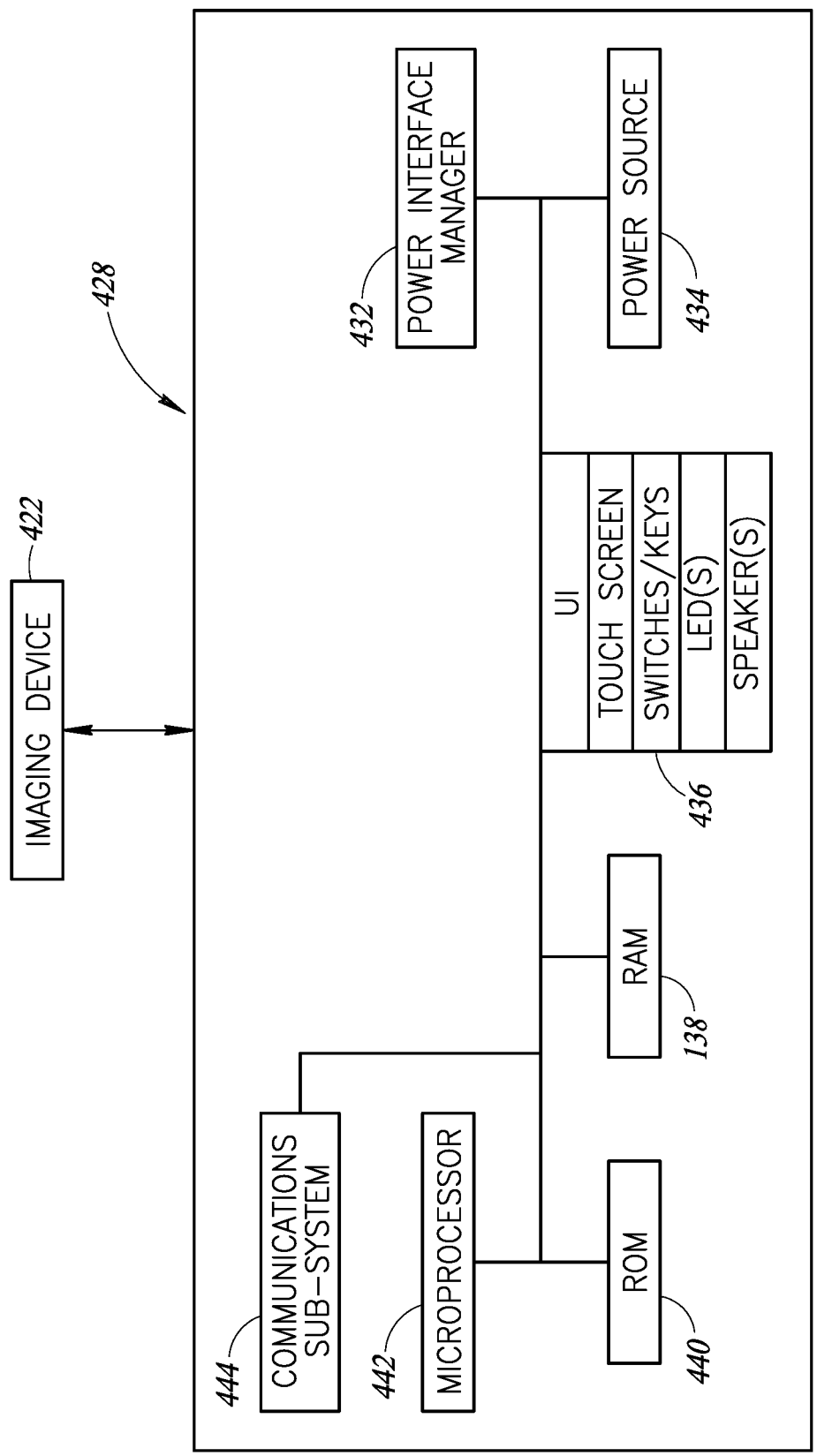
FIG. 5 is a schematic representation of a control unit of the imaging system of FIG. 4.

FIG. 4 further illustrates a control unit 428 in electric communication with the system 400. FIG. 5 illustrates in detail the control unit 428 according to one example, non-limiting implementation. In particular, the control unit 428 is generally operable to provide power to the system 400 and to process or transmit imaging data received from imaging devices 422. FIG. 5 schematically illustrates various control systems, modules, or other sub-systems that operate to control the system 400, including the exchange of data between the imaging devices 422 and the control unit 428.

The control unit 428 includes a controller 442, for example a microprocessor, digital signal processor, programmable gate array (PGA) or application specific integrated circuit (ASIC). The control unit 428 includes one or more non-transitory storage mediums, for example read only memory (ROM) 440, random access memory (RAM) 438, Flash memory (not shown), or other physical computer- or processor-readable storage media. The non-transitory storage mediums may store instructions and/or data used by the controller 442, for example an operating system (OS) and/or applications. The instructions as executed by the controller 442 may execute logic to perform the functionality of the various implementations of the systems 400, 500 described herein, including, but not limited to, capturing and processing data from the imaging devices 422.

In implementations where the system 500 (see FIG. 6) includes a rotating support ring or frame 504, the controller 428 may be communicatively coupled to one or more actuators (not shown) to control rotation of the ring 504. Alternatively, the controller 428 may be communicatively coupled to one or more belts (not shown) for rotating the ring 504. Moreover, the controller 442 may include instructions corresponding to specific positions (i.e. the first position and the second position discussed with reference to FIG. 6), which are transmitted to the actuator or belt for automatically rotating the support ring 504 according to a predetermined manufacturing speed or conveyor speed.

The control unit 428 may include a user interface 436, to allow an end user to operate or otherwise provide input to the systems 400, 500 regarding the operational state or condition of the systems 400, 500. The user interface 436 may include a number of user actuatable controls accessible from the system 400, 500. For example, the user interface 436 may include a number of switches or keys operable to turn the systems 400, 500 ON and OFF and/or to set various operating parameters of the systems 400, 500.

Additionally, or alternatively, the user interface 436 may include a display, for instance a touch panel display. The touch panel display (e.g., LCD with touch sensitive overlay) may provide both an input and an output interface for the end user. The touch panel display may present a graphical user interface, with various user selectable icons, menus, check boxes, dialog boxes, and other components and elements selectable by the end user to set operational states or conditions of the systems 400, 500. The user interface 436 may also include one or more auditory transducers, for example one or more speakers and/or microphones. Such may allow audible alert notifications or signals to be provided to an end user. Such may additionally, or alternatively, allow an end user to provide audible commands or instructions. The user interface 436 may include additional components and/or different components than those illustrated or described, and/or may omit some components.

The switches and keys or the graphical user interface may, for example, include toggle switches, a keypad or keyboard, rocker switches, trackball, joystick or thumbstick. The switches and keys or the graphical user interface may, for example, allow an end user to turn ON the systems 400, 500, start or end a transmittance imaging mode or a interactance imaging mode, communicably couple or decouple to remote accessories and programs, access, transmit, or process imaging data, activate or deactivate motors or audio subsystems, start or end an operational state of a conveyor system, etc.

The control unit 428 includes a communications sub-system 444 that may include one or more communications modules or components which facilitate communications with various components of one or more external device, such as a personal computer or processor, etc. The communications sub-system 444 may provide wireless or wired communications to the one or more external devices. The communications sub-system 444 may include wireless receivers, wireless transmitters or wireless transceivers to provide wireless signal paths to the various remote components or systems of the one or more paired devices. The communications sub-system 444 may, for example, include components enabling short range (e.g., via Bluetooth, near field communication (NFC), or radio frequency identification (RFID) components and protocols) or longer range wireless communications (e.g., over a wireless LAN, Low-Power-Wide-Area Network (LPWAN), satellite, or cellular network) and may include one or more modems or one or more Ethernet or other types of communications cards or components for doing so. The communications sub-system 444 may include one or more bridges or routers suitable to handle network traffic including switched packet type communications protocols (TCP/IP), Ethernet or other networking protocols. In some implementations, the wired or wireless communications with the external device may provide access to look-up table indicative of various material properties and light wavelength properties. For example, an end user may select a material from a variety of materials displayed in the user interface 436, which may be stored in a look-up table or the like in the external device.

The control unit 428 includes a power interface manager 432 that manages supply of power from a power source (not shown) to the various components of the controller 428, for example, the controller 428 integrated in, or attached to the systems 400, 500. The power interface manager 432 is coupled to the controller 442 and a power source. Alternatively, in some implementations, the power interface manager 432 can be integrated in the controller 442. The power source may include external power supply, among others. The power interface manager 432 may include power converters, rectifiers, buses, gates, circuitry, etc. In particular, the power interface manager 432 can control, limit, restrict the supply of power from the power source based on the various operational states of the systems 400, 500.

In some embodiments or implementations, the instructions and/or data stored on the non-transitory storage mediums that may be used by the controller, such as, for example, ROM 440, RAM 438 and Flash memory (not shown), includes or provides an application program interface ("API") that provides programmatic access to one or more functions of the controller 428. For example, such an API may provide a programmatic interface to control one or more operational characteristics of the systems 400, 500, including, but not limited to, one or more functions of the user interface 436, or processing the imaging data received from the imaging device or devices 422. Such control may be invoked by one of the other programs, other remote device or system (not shown), or some other module. In this manner, the API may facilitate the development of third-party software, such as various different user interfaces and control systems for other devices, plug-ins, and adapters, and the like to facilitate interactivity and customization of the operation and devices within the systems 400, 500.

In an example embodiment or implementation, components or modules of the control unit 428 and other devices within the systems 400, 500 are implemented using standard programming techniques. For example, the logic to perform the functionality of the various embodiments or implementations described herein may be implemented as a "native" executable running on the controller, e.g., microprocessor 442, along with one or more static or dynamic libraries. In other embodiments, various functions of the controller 428 may be implemented as instructions processed by a virtual machine that executes as one or more programs whose instructions are stored on ROM 440 and/or random RAM 438. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the control unit 428, such as microprocessor 442, to perform the functions of the control unit 428. The instructions cause the microprocessor 442 or some other processor, such as an I/O controller/processor, to process and act on information received from one or more imaging device(s) 422 to provide the functionality and operations of reconstructing a 3D model based on imaging data.

The embodiments or implementations described above may also use well-known or other synchronous or asynchronous client-server computing techniques. However, the various components may be implemented using more monolithic programming techniques as well, for example, as an executable running on a single microprocessor, or alternatively decomposed using a variety of structuring techniques known in the art, including but not limited to, multiprogramming, multithreading, client-server, or peer-to-peer (e.g., Bluetooth®, NFC or RFID wireless technology, mesh networks, etc., providing a communication channel between the devices within the systems 400, 500), running on one or more computer systems each having one or more central processing units (CPUs) or other processors. Some embodiments may execute concurrently and asynchronously, and communicate using message passing techniques. Also, other functions could be implemented and/or performed by each component/module, and in different orders, and by different components/modules, yet still achieve the functions of the control unit 428.

In addition, programming interfaces to the data stored on and functionality provided by the control unit 428, can be available by standard mechanisms such as through C, C++, C#, and Java APIs; libraries for accessing files, databases, or other data repositories; scripting languages; or Web servers, FTP servers, or other types of servers providing access to stored data. The data stored and utilized by the control unit 428 and overall imaging system may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules within the systems 400, 500 in different ways, yet still achieve the functions of the control unit 428 and imaging systems 400, 500.

Furthermore, in some embodiments, some or all of the components of the control unit 428 and components of other devices within the systems 400, 500 may be implemented or provided in other manners, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use, or provide the contents to perform, at least some of the described techniques.

With reference to FIGS. 4 and 5, the control unit 428 is in electrical communication with the support ring 414 and each of the plurality of imaging devices 422, either through wires 430, which may be internally or externally located with respect to the conveyor system 402, the support 418, and the support ring 414. Alternatively, the control unit 428 may be in wireless communication with the system 400 to wirelessly receive imaging data from imaging devices 422, as described above with reference to FIG. 5. Further, the control unit 428 may be coupled to the system or located external to the system. In an implementation, the control unit 428 provides power to the system 400 and also receives imaging data from the imaging devices 422. The control unit 428 can include at least one processor such as in a standard computer, for processing the imaging data, or alternatively the control unit 428 can transmit the imaging data to an additional external processor or computer that is not specifically illustrated for clarity.

Figure 6:
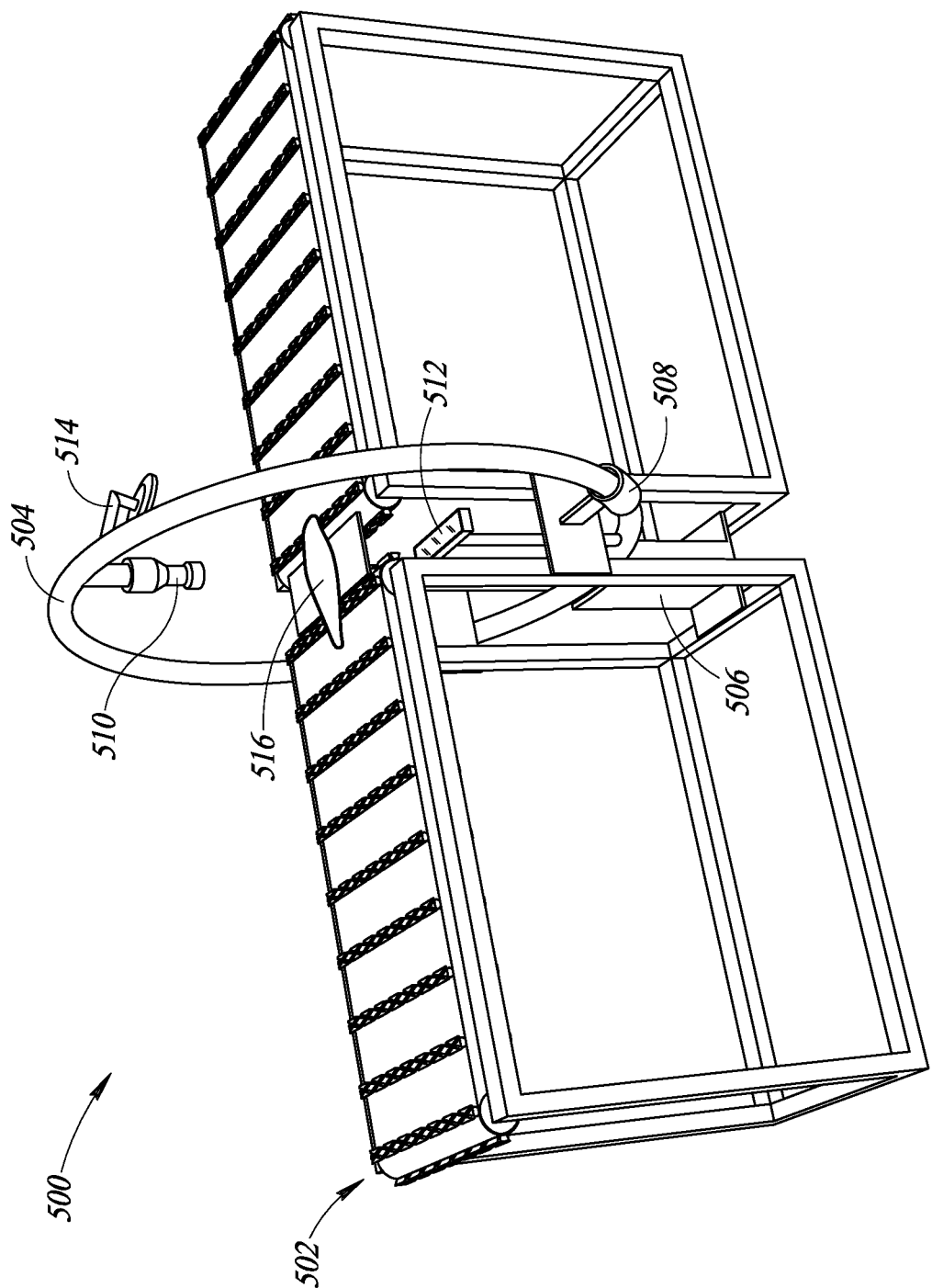
FIG. 6 is a perspective view of an alternative exemplary implementation of an imaging system according to the present disclosure having a support ring and a single imaging device and light source coupled to the support ring, wherein the support ring rotates between at least a first position and second position.

FIG. 6 illustrates an alternative exemplary implementation of an imaging system 500 including a conveyor system 402, a frame or ring 504 coupled to the frame 504, an imaging device 510 coupled to and extending from the frame 504, and a first and second light source 512, 514. Certain features of the implementation of the system 500 are similar or identical to features described above with reference to system 400 and as such, those features have not been repeated in the interest of efficiency.

In this implementation, the frame 504 is coupled to the conveyor system 502 with supports 506, 508, wherein the support 506 is a base with a channel for receiving the frame 504 and at least one collar 508 surrounding the frame 504. However, because this implementation utilizes a single imaging device 510, the system 500 further includes a mechanism for rotating the frame 504 about the conveyor system 502, such that the imaging device 510 can capture imaging data of an object 516 from multiple perspectives, angles, or views to facilitate 3D reconstruction. For example, the base 506 can include a rotating belt in the channel, wherein the belt is in contact with the frame 504 to rotate the frame 504 according to an input received from an external control unit, which may be control unit 428 (see FIG. 4). However, other commercially available mechanisms for rotating the frame 504 are specifically contemplated herein. Moreover, although it is preferable that the frame be rotated automatically, it is possible to base rotation on manual rotation by manipulating collar 508, wherein the collar 508 is adjustable between a closed position that prevents rotation and an open position wherein frame 504 can be rotated.

As such, in this implementation, the frame 504 rotates between at least a first position and a second position, wherein in the first position, the imaging device 510 captures a first set of imaging data corresponding to transmittance or interactance imaging data from the first light source 512 or the second light source 514, respectively. Then, the frame 504 rotates to the second position and repeats the capture process for a second set of imaging data. This process can be repeated to produce as many views from as many orientations as are required for the specific application (i.e. third, fourth, fifth, sixth, or more views based on the imaging device 510 being in different positions with respect to the object 516). Moreover, in implementations where the frame 504 is rotated automatically, rotation of the frame 504 can be done efficiently according to positions established during calibration of the system 500, while reducing the cost of the system 500 due to the use of less imaging devices 510.

Figure 7:
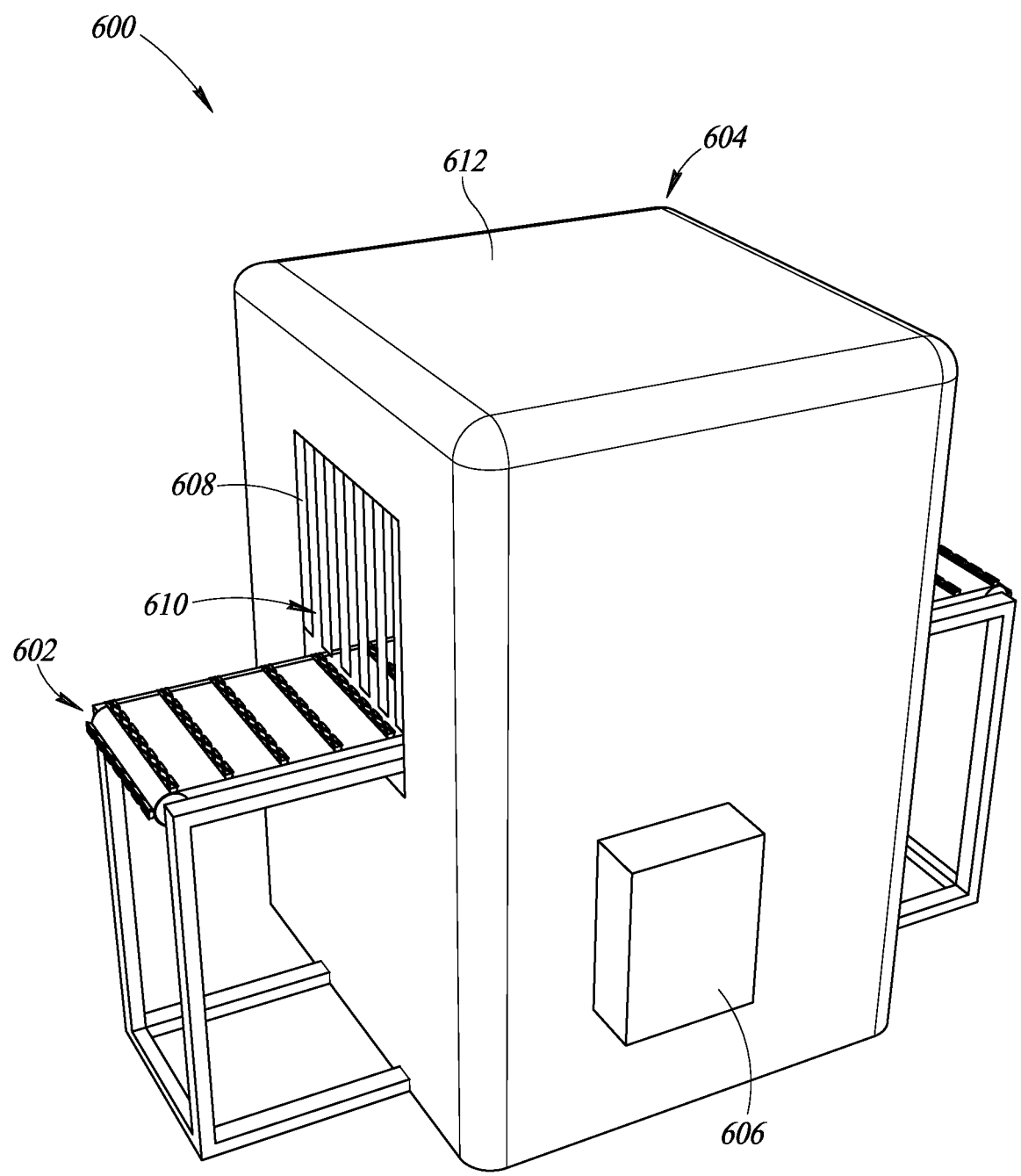
FIG. 7 is a perspective view of an exemplary implementation of an outer housing according to the present disclosure for reducing environmental light to an imaging system within the outer housing.

FIG. 7 illustrates an exemplary representation of a system 600, which may be substantially similar or identical to systems 400, 500, wherein the system 600 includes an outer housing or cover 604, wherein walls 612 of the outer housing 604 are solid and opaque. Entrance portions or openings 610 of the housing 604 include a cover 608 comprising strips of opaque material that extend over at least 80% of an area of each entrance portion 610 such that light cannot enter housing 604. Further, although not specifically illustrated, the support rings or frames 414, 504 can be coupled to and supported by the housing 604 and a control unit 606 can be coupled to an outer wall 612 of the housing 604, wherein the control unit 606 provides power to the system 600, provides coordinates corresponding to positions of the rotating frame 504 and controls rotation of the rotating frame 504, or includes a processor for producing a 3D model based on imaging data received from the system 600, in various implementations.

Figure 8:
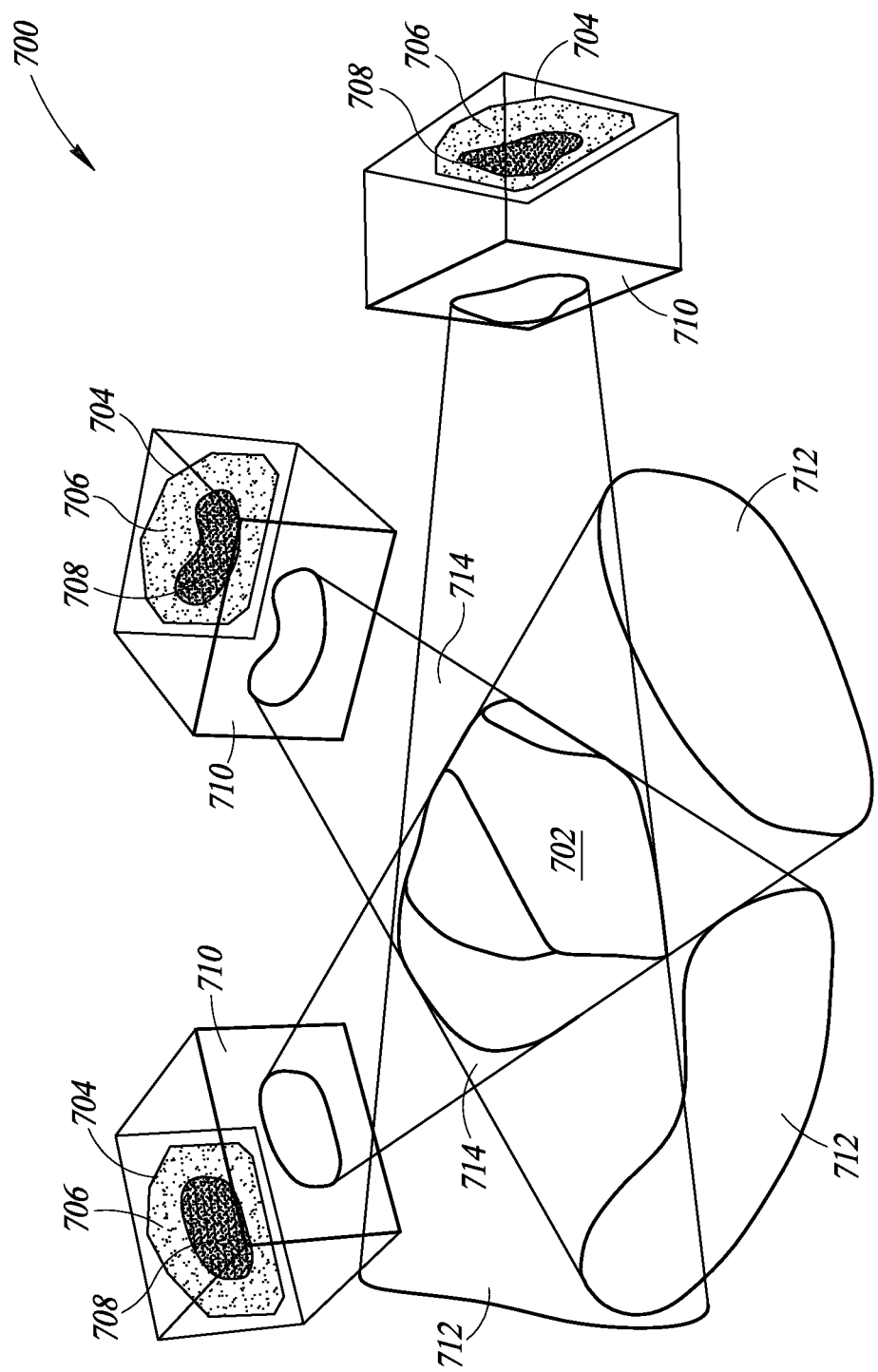
FIG. 8 is a schematic representation of an exemplary implementation of reconstruction of a three-dimensional model from projected silhouettes according to the present disclosure.

FIG. 8 is a schematic representation of a reconstruction method or system 700 utilized by a machine learning system or deep convoluted neural network to produce a 3D model 702 from one-dimensional ("1D") imaging data and two-dimensional ("2D") silhouettes.

In general, machine learning and convolutional neural networks ("CNN") can generally be implemented as a series of operational layers. One or more convolutional layers may be followed by one or more pooling layers, and the one or more pooling layers may be optionally followed by one or more normalization layers. The convolutional layers create a plurality of kernel maps, which are otherwise called filtered images, from a single unknown image. The large quantity of data in the plurality of filtered images is reduced with one or more pooling layers, and the quantity of data is reduced further by one or more rectified linear unit layers ("ReLU") that normalize the data. Preferably, implementations of the present disclosure rely on semantic segmentation wherein the parameters for training the CNN are application dependent and need to be adjusted according to the complexity of the image data, which in turn depends on the food to be inspected.

In other words, the kernels are selected from a known image. Not every kernel of the known image needs to be used by the neural network. Instead, kernels that are determined to be "important" features may be selected. After the convolution process produces a kernel map (i.e., a feature image), the kernel map is passed through a pooling layer, and a normalization (i.e., ReLU) layer. All of the values in the output maps are averaged (i.e., sum & divide), and the output value from the averaging is used as a prediction of whether or not the unknown image contains the particular feature found in the known image.

In the exemplary case, the output value is used to predict whether the unknown image contains the feature of importance, which in an implementation, is a second portion of an object located internal to a first portion of an object, such as the dark meat (i.e. second portion) surrounded by the white meat (i.e. first portion) of a tuna fillet. With this output, the CNN can then produce a silhouette corresponding to the identified areas of interest from an image.

In the illustrated system 700, the machine learning program or deep convolution neural network will receive, as an input, the image data 704 from multiple views captured from systems 400, 500, wherein each image data set corresponds to a photograph of a tuna fillet with a first portion 706 surrounding a second portion 708. While the camera or spectrograph may use a line-scan to acquire 1D data, the 1D data is combined to 2D image data before being used in the CNN to recover the silhouettes, as described herein.

In implementations where the scanned object is a tuna fillet, the first portion 706 corresponds to a first, outer layer of meat with a first set of characteristics and the second portion 708 corresponds to a second, inner layer of meat with a second, different set of characteristics, wherein the second portion 708 is located within the first portion 706. As shown in FIG. 7, each of the image data sets 704 corresponds to imaging data, and preferably transmittance imaging data, which may represent intensity values where brighter pixels are assigned to the first portion 706 and darker pixels are assigned to the second portion 708. As such, the image data 704 is 1D in the sense that it is a single line of a 2D image, or in other words, each pixel or kernel analyzed by the CNN corresponds to an intensity value.

On a highest level of the machine learning program or the deep convolutional neural network, the CNN is trained based on a pool of thousands of representative sample images to identify the general appearance of the second portion 708 (i.e. dark meat in tuna fillets); for instance, the second portion 708 goes through a center of the fillet parallel to its major axis based on a large pool of reference images, which may include thousands of images of tuna fillets. On another level, the CNN will acquire knowledge on edges, lines and curves based on representative sample images, wherein the accuracy of the CNN will improve as more images are scanned. As such, based on the difference in intensity values, the CNN will identify the portions of the photograph that correspond to the second portion 708. Once these portions are identified, the CNN will formulate a plurality of silhouettes 710, wherein each silhouette corresponds to the identified second portion 708 in each of the views represented in 2D.

For example, a CNN is composed of many layers, where layers between the input and output are called "hidden layers." Each layer has numerous neurons, which are fully connected between layers. These connection correspond to weights that are learned based on reference images. A neuron or node is a computational unit that takes an input value, multiplies it with the associated weight, runs it through an activation function (e.g. ReLU as described herein) and delivers an output. This output forms the input of the next neuron linked though another connection. In addition, the CNN can include other layers such as convolutions, pooling, normalization, and dropout that are used similarly to neurons, but have different functions.

Before a network is trained, the connections or weights between nodes are assigned randomly. When training a network, labelled or annotated data is used. For example, the input data (e.g. image data) is correlated with the expected output data (e.g. silhouettes). By providing the input data (e.g. image data) through the input nodes at the first layer, and knowing the expected values of the output layers (e.g. labelled silhouettes), it is possible to adjust the weights of the connections though several iterations, such that whatever the input data is, the CNN returns the expected output. This is basically an optimization process with a large number of parameters. Whenever one weight is changed it will affect the entire network and as such, training a CNN may include tens, hundreds, or thousands of iterations.

The convolution layers of the CNN reduce the size of the image, which determines the area that can be seen or is evaluated. For example, a small window of 9×9 pixels is moved over the full image to be analyzed. In that window, an observer would see a small fraction of the whole object (e.g. lines and corners). As the size of the image is reduced, but the window size is kept the same, more of the object features are recognized. If the image is very small and almost fits in the window, the observer would see the whole fillet as well as the dark meat in a single step.

This is an example of what the neural network sees. In the early layers of the network, weights will be learned that allow for detecting lines and corners that are relevant in identifying the dark meat in a tuna fish fillet, for example. While in the later layers, these lines will form curves, until the whole dark meat is recognized as an object and related to its surrounding as reference (e.g. dark meat is between the boundaries of white meat, runs along the major axis). These features are learned in parallel but are all relevant. Without lines and corners, the dark meat boundaries are difficult to locate based on the overall appearance of dark meat. Similarly, when there are many lines and corners corresponding to dark meat, but the overall appearance of the dark meat is unknown, it is difficult to distinguish which lines and corners are relevant. However, having knowledge of both of these high- and low-level features allows for the detection of the dark meat in the image data.

Then, the computational system back projects each of the silhouettes 710 into a plurality of projections 712 by using an algorithm, wherein in an implementation, the algorithm extends lines corresponding to an outer boundary of each silhouette 710 into a higher dimensional scene, as illustrated in FIG. 7. By back projecting each of the silhouettes 710 and analyzing intersections 714 between projections 712, the 3D model 702 of the second portion 708 can be determined. In an implementation, the back projection is based on a cone shaped field of view. Imaging data corresponding to the interactance imaging mode, such as mode 300, can be utilized to refine the model based on the depth of the object of interest. For example, if the properties of the object of interest are known based on a database of information corresponding to the same, then the amount of light that scatters to be captured in the interactance imaging mode will vary depending on the depth of the object of interest, which in an implementation, is the dark meat in a tuna fillet. Moreover, the interactance imaging data assists with correcting for concavities in the surface of the scanned object because the captured light will vary according to the depth the object, as above. As such, if the object has a concavity, the interactance imaging data will differ for the portion of the object with the concavity, where the material is thinner as opposed to the portion of the object without the concavity, where the material is thicker (i.e. a lower captured intensity value corresponds to thinner material because less of the light will be scattered and captured and a higher intensity value corresponds to thicker material because more of the light will be scattered when it cannot penetrate or transmit through the thicker material).

Figure 9:
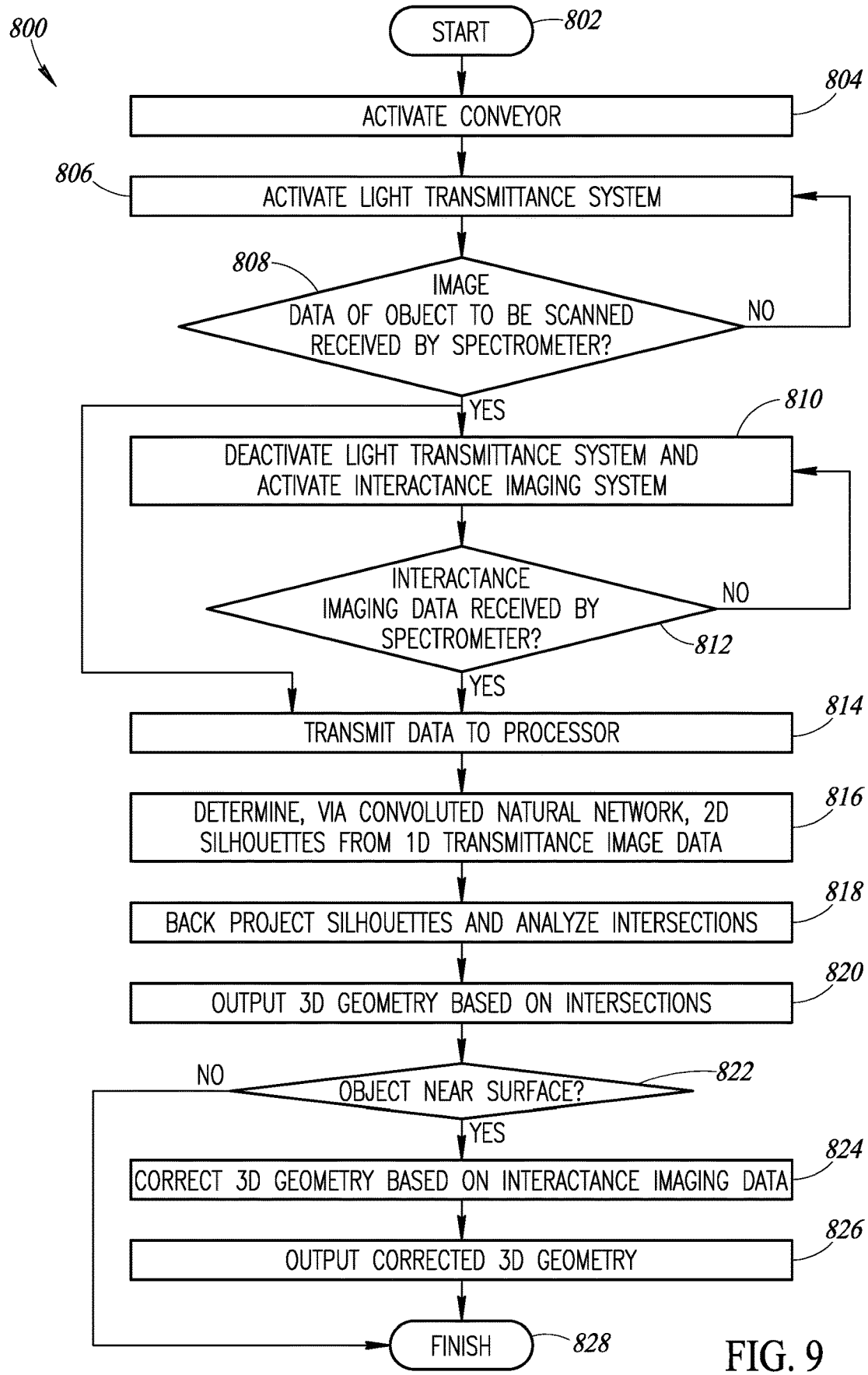
FIG. 9 is a flow diagram of an exemplary implementation of a method according to the present disclosure for capturing and processing image data of an object to determine boundaries of an inner portion of the object.

FIG. 9 is a flow diagram representing an exemplary method 800 of generating a 3D model of an object of interest based on image data captured by an imaging system (e.g., imaging systems 400, 500). The method 800 begins at 802 wherein a conveyor is activated at 804 and an object to be scanned is loaded onto the conveyor. Activation of the conveyor can occur through an external switch, or through a control unit or program. Similarly, at 806, the light transmittance system, which may be substantially similar to the transmittance imaging mode 200 described with reference 200, is activated, either manually via an external switch or through a control unit or processor. An imaging device that is part of the light transmittance system, either on its own or through a program associated with a control unit in electronic communication with the transmittance system, determines at 808 whether transmittance image data is received by the imaging device corresponding to light passing through the object on the conveyor, wherein in an implementation, the imaging device is a spectrograph, camera, or sensor.

If no image data is received, the process returns to 806 and repeats until image data is received. Once transmittance image data is received, it is transmitted to a processor and the method 800 proceeds to 810, wherein the transmittance mode is deactivated and the interactance imaging mode is activated. The interactance imaging mode may be substantially similar to the interactance mode 300 described with reference to FIG. 3. Again, it is determined at 812 whether the imaging device or spectrograph receives interactance imaging data. If not, the process repeats by returning to 810 until the imaging device receives interactance imaging data. Once the interactance imaging data is detected, the interactance imaging data is transmitted to the processor at 814. In implementations where there are multiple imaging devices, the above process can be repeated for each unique imaging device to produce a plurality of views. Alternatively, in implementations where the imaging device rotates, this process is repeated each time the imaging device is located in a unique position in order to generate a plurality of views or a plurality of transmittance imaging data sets and a plurality of interactance imaging data sets.

The processor includes a machine learning program or a CNN, wherein the CNN receives as an input, the transmittance image data corresponding to each view at 816. The CNN then generates at 816, a plurality of silhouettes corresponding to a feature of interest in each transmittance image data set, which in an implementation, is an object located within a piece of food, or a second portion of fish located within a first portion of fish. Each of the silhouettes is back projected at 818 into a plurality of projections and the common intersections of each projection are analyzed to determine a 3D geometry based on the intersections. The processor then outputs this 3D geometry at 822 and it is determined, either manually or through an additional processor step, whether the object of interest is near a surface of the scanned object. If not, the 3D geometry, based on the transmittance imaging data, is output and the method 800 finishes at 828.

If the object of interest is near the surface, the process continues to 824, wherein the CNN uses the interactance imaging data to correct or clarify the 3D geometry based on the transmittance image data. Once the 3D geometry is corrected at 824, the processor or the CNN outputs the corrected 3D geometry at 826 and the process finishes at 828.

Figure 10:
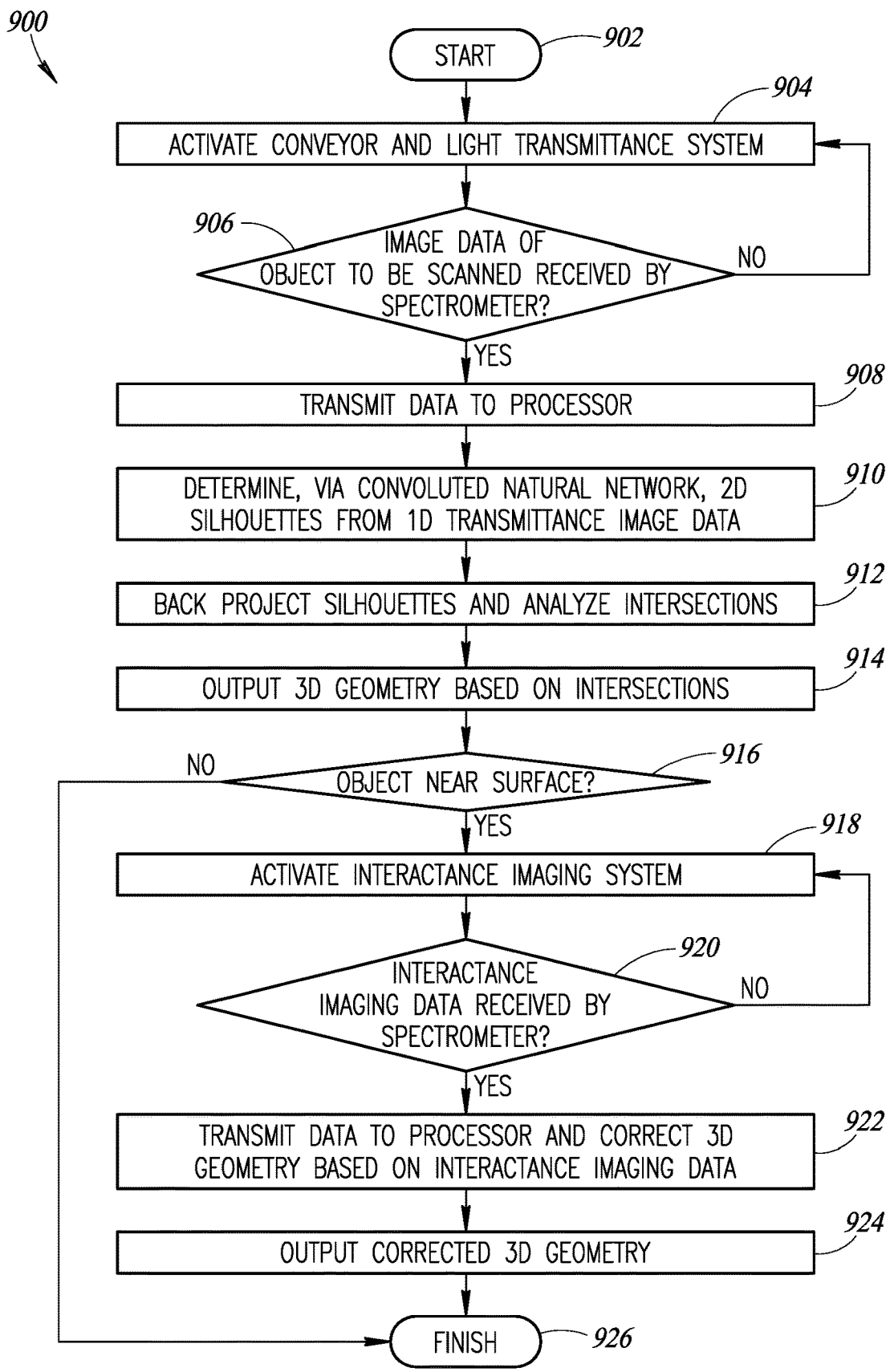
FIG. 10 is a flow diagram of an alternative exemplary implementation of a method according to the present disclosure for capturing and processing image data of an object to determine boundaries of an inner portion of the object.

FIG. 10 is an alternative exemplary implementation of a method 900 for generating a 3D model of an object of interest based on image data captured by an imaging system. The method 900 begins at 902, wherein a conveyor and light transmittance system 904 are activated. The imaging device or spectrograph determines at 906 whether imaging data corresponding to transmittance imaging data is received or captured by the imaging device. If not, the processor returns to 904 until the data is received. If so, the method 900 continues to 908, wherein the transmittance imaging data is transmitted to a processor at 908. The processor then determines, via a convoluted neural network, a plurality of 2D silhouettes from the 1D transmittance image data at 910. Each of the silhouettes are back projected and the intersections are analyzed at 912. Then, the processor outputs a 3D geometry based on common intersections between each of the projections at 914.

Then, it is determined at 916 with the processor or the CNN, whether an object of interest is near the surface of the scanned object. If not, the method 900 finishes at 926 with the 3D model based on the transmittance imaging data. If yes, the method 900 continues to activate the interactance imaging system at 918, wherein the imaging device determines whether imaging data corresponding to interactance imaging data is received by the imaging device or spectrograph at 920. If not, the method 900 returns to 918 until such data is received or captured. if so, the method 900 proceeds to 922, wherein the interactance imaging data is transmitted to the processor and the 3D model is corrected, if necessary, based on the interactance imaging data. Finally, the corrected 3D model is outputted at 924 and the method 900 finishes at 926.

Through the acquisition of three-dimensional information, the present disclosure allows for more precisely determining the volume and shape of internal defects, which may have impacts on quality control inspections as to whether or not certain food material needs to be rejected. Further, by knowing the three-dimensional geometry of the objects, processing and removal of secondary products can be performed more accurately and thus minimizes the loss of primary products.

The above description of illustrated implementations, including what is described in the Abstract, is not intended to be exhaustive or to limit the implementations to the precise forms disclosed. Although specific implementations of and examples are described herein for illustrative purposes, various equivalent modifications can be made without departing from the spirit and scope of the disclosure, as will be recognized by those skilled in the relevant art. The teachings provided herein of the various implementations can be applied outside of the food processing context, and not necessarily the exemplary imaging systems and methods generally described above.

For instance, the foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "computer-readable medium" can be any element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other nontransitory media.

Many of the methods described herein can be performed with variations. For example, many of the methods may include additional acts, omit some acts, and/or perform acts in a different order than as illustrated or described.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the implementations can be modified, if necessary to employ concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:
1. A system, comprising:
a first conveyor;
a second conveyor separated from the first conveyor by a gap;
a transparent plate positioned in the gap and coupled to at least one of the first conveyor and the second conveyor;
a support ring positioned at least in part in the gap and coupled to at least one of the first conveyor and the second conveyor, the support ring aligned with the transparent plate and extending around the transparent plate, the support ring structured to rotate around the transparent plate;
an opening through the support ring, the transparent plate extending through the opening;
at least one imaging device coupled to the support ring;
a first light source coupled to the support ring; and
a control unit in electronic communication with the support ring and the at least one imaging device,
wherein during operation, the support ring rotates between at least a first position and a second position and the first light source emits light directed towards an object on the transparent plate in the first position and the second position and the control unit receives imaging data from the at least one imaging device, the control unit constructing a 3D model of a second portion of the object contained within a first portion of the object.

2. The system of claim 1 wherein the at least one imaging device transmits imaging data to the control unit, the imaging data including one of interactance imaging data and transmittance imaging data.

3. The system of claim 1 wherein the object is a tuna fillet and the first light source emits light at a wavelength that is equal to one of approximately 1260 nanometers, approximately 805 nanometers, or approximately 770 nanometers.

4. The system of claim 1 wherein the processor uses machine learning in the form of a convolutional neural network to process the imaging data.

5. The system of claim 4 wherein the convolutional neural network receives the image data and outputs a plurality of silhouettes based on the image data corresponding to the second portion of the object, the processor projecting the silhouettes into a plurality of projections and analyzing an intersection between the plurality of projections to construct the 3D model.

6. The system of claim 1 wherein the at least one imaging device includes a plurality of cameras coupled to the support ring, each of the plurality of cameras capturing one of transmittance, interactance, or reflectance imaging data from the first light source.

7. The system of claim 6 wherein the support ring includes a second light source coupled to the support ring, wherein during operation, the second light source emits light directed to the transparent plate.

8. A device, comprising:
a conveyor having a space between a first portion and a second portion of the conveyor;
a plate positioned in the space and coupled to the conveyor;
a support ring positioned at least in part in the space and coupled to the conveyor, the support ring aligned with the plate and extending around the plate with the plate extending through the support ring;
at least one light source coupled to the support ring;
an imaging device coupled to the support ring; and
a processor in electronic communication with the imaging device,
wherein during operation, the support ring rotates between at least a first position and a second position and the at least one light source emits light in a first direction towards an object on the plate and the imaging device receives light from the at least one light source after the light passes through the object, wherein the processor receives a first set of image data from the imaging device when the support ring is in the first position and a second set of image data from the imaging device when the support ring is in the second position and outputs a 3D model of an inner portion of the object from the first set of image data and the second set of image data, wherein at least one of the first set of image data and the second set of image data are interactance image data corresponding to light from the at least one light source that passes through the object, and is reflected in a second direction different than the first direction to be received at the imaging device.

9. The device of claim 8 wherein the processor utilizes machine learning to process the first set of image data and the second set of image data into a plurality of silhouettes and to project the plurality of silhouettes into a plurality of projections, wherein the three-dimensional model is based on an intersection between each of the plurality of projections.

10. The device of claim 8 further comprising a second light source coupled to the support ring, the imaging device capturing a third set of image data from the second light source when the support ring is in the first or second position, the processor utilizing the third set of image data to clarify boundaries of the three-dimensional model.

11. The device of claim 8 wherein the imaging device is a spectrograph and the at least one light source emits light at a wavelength selected from one of approximately 1260 nanometers, approximately 805 nanometers, or approximately 770 nanometers.

12. A method, comprising:
emitting light from a light source at a first instance, the emitting including directing the light through an object having a first portion and a second portion, the second portion enclosed within the first portion;

capturing light from the light source after the light passes through the object with a first imaging device positioned below the object, the captured light corresponding to transmittance image data of the first portion and the second portion received by the first imaging device;

rotating a support ring coupled to the light source to change a position of the light source from a first position corresponding to the first instance to a second position different from the first position;

emitting light from the light source at a second instance toward the object, including emitting light with the light source in the second position;

capturing light from the light source after the light is backscattered by the object with a second imaging device positioned above the object, the captured light corresponding to interactance image data of the first portion and the second portion received by the second imaging device;

transmitting the transmittance image data to a processor;

analyzing the transmittance image data with the processor to detect a boundary between the first portion and the second portion, wherein the analyzing includes utilizing machine learning to produce a three dimensional representation of the second portion internal to the first portion; and refining the three dimensional representation of the second portion with the interactance image data, including adjusting the three dimensional representation based on a depth of the second portion of the object relative to the first portion.

13. The method of claim 12 wherein emitting light from the light source at the first instance includes emitting the light with a wavelength selected from one of approximately 1260 nanometers, 805 nanometers, or 770 nanometers.

14. The method of claim 12 wherein utilizing machine learning to produce the three dimensional representation of the second portion includes the machine learning utilizing a deep convolutional neural network for processing the image data.

15. The method of claim 12 wherein analyzing the image data with the processor includes utilizing machine learning to output a plurality of two dimensional silhouettes corresponding to the image data of the second portion.

16. The method of claim 15 wherein analyzing the image data with the processor includes utilizing machine learning to create a plurality of projections, wherein each projection corresponds to a respective one of the plurality of two dimensional silhouettes.

17. The method of claim 15 wherein analyzing includes utilizing machine learning to produce a three dimensional representation further includes analyzing an intersection between each of the plurality of projections to output a three dimensional representation of the second portion of the object.

18. The system of claim 1 wherein a position of the transparent plate with respect to the first conveyor and the second conveyor is fixed and static.

19. The method of claim 12 wherein refining the three dimensional representation includes correcting the three dimensional representation for concavities in a surface of the object with the interactance image data.

* * * * *